(12) United States Patent
Yamamura et al.

(10) Patent No.: US 10,782,290 B2
(45) Date of Patent: Sep. 22, 2020

(54) METHOD FOR PREDICTING POST-THERAPY PROGNOSIS OF RELAPSING-REMITTING MULTIPLE SCLEROSIS (RRMS) PATIENT, AND METHOD FOR DETERMINING APPLICABILITY OF NOVEL THERAPY

(71) Applicants: CHUGAI SEIYAKU KABUSHIKI KAISHA, Tokyo (JP); National Center of Neurology and Psychiatry, Tokyo (JP)

(72) Inventors: Takashi Yamamura, Tokyo (JP); Masakazu Nakamura, Tokyo (JP)

(73) Assignees: National Center of Neurology and Psychiatry (JP); Chugai Seiyaku Kabushiki Kaisha (JP)

( * ) Notice: Subject to any disclaimer, the term of this patent is extended or adjusted under 35 U.S.C. 154(b) by 529 days.

(21) Appl. No.: 14/897,498

(22) PCT Filed: Jun. 11, 2014

(86) PCT No.: PCT/JP2014/065449
§ 371 (c)(1),
(2) Date: Dec. 10, 2015

(87) PCT Pub. No.: WO2014/200018
PCT Pub. Date: Dec. 18, 2014

(65) Prior Publication Data
US 2016/0139117 A1   May 19, 2016

(30) Foreign Application Priority Data
Jun. 11, 2013  (JP) .................... 2013-122845

(51) Int. Cl.
*G01N 33/564*  (2006.01)
*A61K 45/00*  (2006.01)
(Continued)

(52) U.S. Cl.
CPC ........... *G01N 33/564* (2013.01); *A61K 45/00* (2013.01); *C07K 16/2866* (2013.01);
(Continued)

(58) Field of Classification Search
CPC ............ G01N 33/564; G01N 33/5052; G01N 2333/5412; G01N 2333/565;
(Continued)

(56) References Cited

U.S. PATENT DOCUMENTS 5,126,250 A  6/1992  McDonough et al.
5,670,373 A  9/1997  Kishimoto
(Continued)

FOREIGN PATENT DOCUMENTS

AR  068564  11/2009
CA  1332367  10/1994
(Continued)

OTHER PUBLICATIONS

Chihara et al. Interleukin 6 signaling promotes anti-aquaporin 4 autoantibody production from plasmablasts in neuromyelitis optica. PNAS. 108 (9): 3701-3706 (Mar. 1, 2011) IDS.*
(Continued)

*Primary Examiner* — Gailene Gabel
(74) *Attorney, Agent, or Firm* — Klarquist Sparkman, LLP

(57) ABSTRACT

According to the present invention, the amount of a plasmablast (PB) in a sample of a relapsing-remitting multiple sclerosis (RRMS) patient can be measured, thereby predicting the therapeutic effect of interferon beta (IFN-β) or predicting a RRMS case for which the continuous administration of IFN-β is difficult due to the manifestation of a serious adverse reaction or the aggravation of concomitant immune disorder. In addition, the amount of PB in a sample of a RRMS patient can also be measured, thereby predicting the therapeutic effect of an IL-6 inhibitor in the treatment of RRMS. As a result, a treatment method effective for patients not suitable for IFN-β in the treatment of RRMS can be provided.

7 Claims, 8 Drawing Sheets

(51) Int. Cl.
*C07K 16/28* (2006.01)
*G01N 33/50* (2006.01)

(52) U.S. Cl.
CPC ..... *G01N 33/5052* (2013.01); *C07K 2317/76* (2013.01); *G01N 2333/5412* (2013.01); *G01N 2333/565* (2013.01); *G01N 2333/70596* (2013.01); *G01N 2800/285* (2013.01); *G01N 2800/52* (2013.01)

(58) Field of Classification Search
CPC ..... G01N 2333/70596; G01N 2800/52; G01N 2800/285; A61K 45/00; C07K 16/2866; C07K 2317/76
See application file for complete search history.

(56) References Cited

U.S. PATENT DOCUMENTS

| | | | |
|---|---|---|---|
| 5,817,790 | A | 10/1998 | Tsuchiya et al. |
| 6,309,636 | B1 | 10/2001 | Do Couto et al. |
| 6,723,319 | B1 | 4/2004 | Ito et al. |
| 7,955,590 | B2 | 6/2011 | Gillies et al. |
| 8,017,121 | B2 | 9/2011 | Kishimoto et al. |
| 8,398,980 | B2 | 3/2013 | Kano et al. |
| 8,470,316 | B2 | 6/2013 | Yasunami |
| 8,562,991 | B2 | 10/2013 | Igawa et al. |
| 8,623,355 | B2 | 1/2014 | Okada et al. |
| 8,771,686 | B2 | 7/2014 | Ishida |
| 8,945,558 | B2 | 2/2015 | Kobara |
| 9,017,677 | B2 | 4/2015 | Mihara |
| 9,260,516 | B2 | 2/2016 | Nishimoto et al. |
| 2002/0187150 | A1 | 12/2002 | Mihara et al. |
| 2004/0018540 | A1 | 1/2004 | Yamamura et al. |
| 2004/0071706 | A1 | 4/2004 | Kishimoto et al. |
| 2005/0142635 | A1 | 6/2005 | Tsuchiya et al. |
| 2005/0158317 | A1 | 7/2005 | Blay et al. |
| 2006/0134113 | A1 | 6/2006 | Mihara |
| 2006/0292147 | A1 | 12/2006 | Yoshizaki et al. |
| 2007/0036785 | A1 | 2/2007 | Kishimoto et al. |
| 2007/0148169 | A1 | 6/2007 | Yoshizaki et al. |
| 2007/0280945 | A1 | 12/2007 | Stevens et al. |
| 2009/0269335 | A1 | 10/2009 | Nakashima et al. |
| 2009/0291076 | A1 | 11/2009 | Morichika et al. |
| 2009/0324589 | A1 | 12/2009 | Igawa et al. |
| 2010/0061986 | A1 | 3/2010 | Takahashi |
| 2010/0129357 | A1 | 5/2010 | Garcia-Martinez et al. |
| 2010/0316636 | A1 | 12/2010 | Radin et al. |
| 2011/0076275 | A1 | 3/2011 | Igawa et al. |
| 2011/0098450 | A1 | 4/2011 | Igawa et al. |
| 2011/0150869 | A1 | 6/2011 | Mitsunaga |
| 2011/0245473 | A1 | 10/2011 | Igawa et al. |
| 2012/0183539 | A1 | 7/2012 | Maeda |
| 2012/0253016 | A1 | 10/2012 | Igawa et al. |
| 2012/0301460 | A1 | 11/2012 | Bao et al. |
| 2013/0202588 | A1 | 8/2013 | Nishimura |
| 2013/0317203 | A1 | 11/2013 | Igawa et al. |
| 2015/0166666 | A1 | 6/2015 | Igawa et al. |
| 2016/0022812 | A1 | 1/2016 | Mitsunaga et al. |
| 2016/0139117 | A1 | 5/2016 | Yamamura et al. |
| 2017/0121412 | A1 | 5/2017 | Igawa et al. |
| 2018/0148509 | A1 | 5/2018 | Kakehi et al. |
| 2018/0149573 | A1* | 5/2018 | Yamamura ........... A61K 39/395 |
| 2019/0085085 | A1 | 3/2019 | Igawa et al. |

FOREIGN PATENT DOCUMENTS

| | | |
|---|---|---|
| CA | 2523577 | 11/2004 |
| CA | 2560953 | 9/2005 |
| CA | 2625773 | 4/2007 |
| CA | 2626688 | 4/2007 |
| CA | 2648644 | 10/2007 |
| CA | 2700394 | 4/2009 |
| CA | 2700498 | 4/2009 |
| CA | 2203182 | 11/2009 |
| CA | 2549467 | 12/2012 |
| CA | 2443294 | 9/2013 |
| CN | 101849006 | 9/2010 |
| CN | 103476793 | 12/2013 |
| EP | 0361902 | 4/1990 |
| EP | 0628639 | 12/1994 |
| EP | 0783893 | 7/1997 |
| EP | 0791359 | 8/1997 |
| EP | 0983767 | 3/2000 |
| EP | 1004315 | 5/2000 |
| EP | 1074268 | 2/2001 |
| EP | 1334731 | 8/2003 |
| EP | 1 374 900 | 1/2004 |
| EP | 1690550 | 8/2006 |
| EP | 1707215 | 10/2006 |
| EP | 1728801 | 12/2006 |
| EP | 1733740 A1 | 12/2006 |
| EP | 1941907 | 7/2008 |
| EP | 1941908 | 7/2008 |
| EP | 1967207 | 9/2008 |
| EP | 1967209 | 9/2008 |
| EP | 1 990 060 | 11/2008 |
| EP | 2123302 | 11/2009 |
| EP | 2174667 | 4/2010 |
| EP | 2194066 | 6/2010 |
| EP | 2196220 | 6/2010 |
| EP | 2202245 | 6/2010 |
| EP | 2206775 | 7/2010 |
| EP | 2275443 | 1/2011 |
| EP | 2305306 | 4/2011 |
| EP | 2578233 | 4/2013 |
| EP | 2639305 | 9/2013 |
| EP | 2330193 | 6/2015 |
| EP | 3263132 | 1/2018 |
| JP | H02-163096 | 6/1990 |
| JP | 2004-028926 | 1/2004 |
| RU | 2147442 | 4/2000 |
| RU | 2195960 | 1/2003 |
| RU | 2430111 | 9/2011 |
| TW | 2010/21829 | 6/2010 |
| WO | WO 92/19759 | 11/1992 |
| WO | WO 1996/011020 | 4/1996 |
| WO | WO 1996/012503 | 5/1996 |
| WO | WO 98/42377 | 10/1998 |
| WO | WO 99/08707 | 2/1999 |
| WO | WO 99/47170 | 9/1999 |
| WO | WO 99/58572 | 11/1999 |
| WO | WO 02/34292 | 5/2002 |
| WO | WO 02/080969 | 10/2002 |
| WO | WO 2004/096273 | 11/2004 |
| WO | WO 2005/037315 | 4/2005 |
| WO | WO 2005/061000 | 7/2005 |
| WO | WO 2005/080429 | 9/2005 |
| WO | WO 2005/090405 | 9/2005 |
| WO | WO 2006/023144 | 3/2006 |
| WO | WO 2006/070286 | 7/2006 |
| WO | WO 2006/072954 | 7/2006 |
| WO | WO 2006/119115 | 11/2006 |
| WO | WO 2007/043641 | 4/2007 |
| WO | WO 2007/046489 | 4/2007 |
| WO | WO 2007/058194 | 5/2007 |
| WO | WO 2007/061029 | 5/2007 |
| WO | WO 2007/074880 | 7/2007 |
| WO | WO 2007/086490 | 8/2007 |
| WO | WO 2007/114319 | 10/2007 |
| WO | WO 2007/116962 | 10/2007 |
| WO | WO 2007/137984 | 12/2007 |
| WO | WO 2007/143168 | 12/2007 |
| WO | WO 2008/020079 | 2/2008 |
| WO | WO 2008/090901 | 7/2008 |
| WO | WO 2009/010539 | 1/2009 |
| WO | WO 2009/014263 | 1/2009 |
| WO | WO 2009/041613 | 4/2009 |
| WO | WO 2009/041621 | 4/2009 |
| WO | WO 2009/041643 | 4/2009 |
| WO | WO 2009/044774 | 4/2009 |
| WO | WO 2009/125825 | 10/2009 |
| WO | WO 2009/148148 | 12/2009 |
| WO | WO 2010/035769 | 4/2010 |

(56) References Cited

FOREIGN PATENT DOCUMENTS

| | | |
|---|---|---|
| WO | WO 2010/065078 | 6/2010 |
| WO | WO 2010/107108 | 9/2010 |
| WO | WO 2011/013786 | 2/2011 |
| WO | WO 2011/149046 | 12/2011 |
| WO | WO 2011/149051 | 12/2011 |
| WO | WO 2012/063875 | 5/2012 |
| WO | WO 2012/064627 | 5/2012 |
| WO | WO 2012/118750 | 9/2012 |
| WO | WO 2014/200018 | 12/2014 |
| WO | WO 2016/136933 | 9/2016 |
| WO | WO 2016/186154 | 11/2016 |
| WO | WO 2018/203545 | 11/2018 |

OTHER PUBLICATIONS

Balint et al. Alterations of the peripheral B cell compartment in pediatric-onset multiple sclerosis. Journal of Neurology. vol. 258, Suppl 1, pp. S202, Abstract No. P732 (May 2011).*
Akira et al., "Interleukin-6 in Biology and Medicine," *Adv. Immunol.*, vol. 54:1-78, 1993.
Araki et al., "Clinical Improvement in a Patient with Neuromyelitis Optica following Therapy with the Anti-IL-6 Receptor Monoclonal Antibody Tocilizumab," *Mod. Rheumatol.*, vol. 23:827-831, 2013.
Aricha et al., "Blocking of IL-6 Suppresses Experimental Autoimmune Myasthenia Gravis," *J. Autoimmun.*, vol. 36:135-141, 2011.
Annual Report 2012 (Integrated Edition including CSR Report), Chugai Pharmaceutical Co. Ltd., Mar. 27, 2013.
Bromberg, The IL-6/Jak/Stat3 Pathway: Targeting Metastatic Breast Cancer Research Update, online publication, Mar. 1, 2009.
De Vita et al., "Serum levels of interleukin-6 as a prognostic factor in advanced non-small cell lung cancer," *Oncol Rep* vol. 5(3):649-652, 1998.
Hirano et al., "Complementary DNA for a Novel Human Interleukin (BSF-2) that Induces B Lymphocytes to Produce Immunoglobulin," *Nature*, vol. 324:73-76, 1986.
Hirata et al., "Characterization of IL-6 Receptor Expression by Monoclonal and Polyclonal Antibodies," *J. Immunol.*, vol. 143:2900-2906, 1989.
Huang and Vitetta, "A Monoclonal Anti-Human IL-6 Receptor Antibody Inhibits the Proliferation of Human Myeloma Cells," *Hybridoma*, vol. 12:621-630, 1993.
Krieckaert et al., "Immunogenicity of Biologic Therapies—We Need Tolerance," *Nat. Rev. Rheumatol.*, vol. 10:558-559, 2010.
Lotz et al., "B Cell Stimulating Factor 2/Interleukin 6 is a Costimulant for Human Thymocytes and T Lymphocytes," *J. Exp. Med.*, vol. 167:1253-1258, 1988.
Nishimoto et al., "Humanized Anti-Interleukin-6 Receptor Antibody Treatment of Multicentric Castleman Disease," *Blood*, vol. 106:2627-2632, 2005.
Novick et al., "Monoclonal Antibodies to the Soluble Human IL-6 Receptor: Affinity Purification, ELISA, and Inhibition of Ligand Binding," *Hybridoma*, vol. 10:137-146, (1991).
Okabe, Proprietary Innovative Antibody Engineering Technologies in Chugai Pharmaceutical, Dec. 18, 2012.
Reichert, "Antibodies to Watch in 2014," *mAbs*, vol. 6:799-802, 2014.
Taga et al., "Receptors for B Cell Stimulatory Factor 2," *J. Exp. Med.*, vol. 166: 967-981, 1987.
Taga et al., "Interleukin-6 Triggers the Association of its Receptor with a Possible Signal Transducer, gp130," *Cell*, vol. 58:573-581, 1989.
Yamasaki et al., "Cloning and Expression of the Human Interleukin-6 (BSF-2/IFNβ2) Receptor," *Science*, vol. 241:825-828, 1988.
Bromberg, "The IL-6/Jak/Stat3 Pathway: Targeting Metastatic Breast Cancer Research Update," www.mountainsofhopefoundation.org, 2009 (4 pages).
De Vita et al., "Serum levels of interleukin-6 as a prognostic factor in advanced non-small cell lung cancer," *Oncology Reports* 5:649-652, 1998.
Nakamura et al., "Plasmablast in the pathology of multiple sclerosis," *Jpn J Clin Immunol*, 38(5):403-411, 2015.
Abiatari et al., "Consensus Transcriptome Signature of Perineural Invasion in Pancreatic Carcinoma," *Mol. Cancer Ther.*, vol. 8:1494-1504, 2009.
Besse et al., "Phase 2 Study of Frontline Bortezomib in Patients with Advanced Non-Small Cell Lung Cancer," *Lung Cancer*, vol. 76:78-83, 2012.
Demir et al., "Nerve-Cancer Interactions in the Stromal Biology of Pancreatic Cancer," *Front. Physiol.*, vol. 3:1-11, 2012.
Kayahara et al., "The Nature of Neural Invasion by Pancreatic Cancer," Pancreas, vol. 35:218-223, 2007.
Koide et al., "Establishment of Perineural Invasion Models and Analysis of Gene Expression Revealed an Invariant Chain (CD74) as a Possible Molecule Involved in Perineural Invasion in Pancreatic Cancer," *Clin. Cancer Res.*, vol. 12:2419-2426, 2006.
Li et al., "Phase II Study of the Proteasome Inhibitor Bortezomib (PS-341, Velcade®) in Chemotherapy-Naïve Patients with Advanced Stage in Non-Small Cell Lung Cancer (NSCLC)," *Lung Cancer*, vol. 68:89-93, 2010.
Märten et al, "Bortezomib is Ineffective in an Orthotopic Mouse Model of Pancreatic Adenocarcinoma," *Mol. Cancer Ther.*, vol. 7:3624-3631, 2008.
Nakamura et al., "Plasmablast in the Pathology of Multiple Sclerosis," *Jpn. J. Clin. Immunol.*, vol. 38:403-411, 2015.
National Cancer Institute, "SEER Cancer Stat Facts: Pancreas Cancer," https://seer.cancer.gov/statfacts/html/pancreas.html, National Cancer Institute, Bethesda, Maryland, United States, accessed Apr. 25, 2017 (9 pages).
Ozaki et al., "The Prognostic Significance of Lymph Node Metastasis and Intrapancreatic Perineural Invasion in Pancreatic Cancer After Curative Resection," *Jpn. J. Surg.*, vol. 29:16-22, 1999.
Wang et al., "Phase II Study of Panobinostat and Bortezomib in Patients with Pancreatic Cancer Progressing on Gemcitabine-Based Therapy," *Anticancer Res.*, vol. 32:1027-1032, 2012.
Japanese Society of Neurological Therapeutics, "Standard Neurological Therapeutics: Neuromyelitis Optica (NMO)," vol. 30, No. 6, pp. 777-794, 2003 (including a partial English translation).
Polman et al., "Diagnostic Criteria for Multiple Sclerosis: 2010 Revisions to the McDonald Criteria," *Ann Neurol* 69:292-302, 2011.
Wingerchuk et al., "Revised diagnostic criteria for neuromyelitis optica," *Neurology* 66:1485-1489, 2006.
Wingerchuk et al., "International consensus diagnostic criteria for neuromyelitis optica spectrum disorders," *Neurology* 85:177-189, 2015.
Akari et al., "Efficacy of the Anti-IL-6 Receptor Antibody Tocilizumab in Neuromyelitis Optica," *Neurology*, vol. 82:1302-1306, 2014.
Barkhof et al., "Comparison of MRI Criteria at First Presentation to Predict Conversion to Clinically Definite Multiple Sclerosis," *Brain*, vol. 120:2059-2069, 1997.
Chihara et al., "Interleukin 6 Signaling Promotes Anti-Aquaporin 4 Autoantibody Production from Plasmablasts in Neuromyelitis Optica," *Proc. Nat. Acad. Sci. U.S.A.*, vol. 108:3701-3706, 2011.
Chihara et al., "Autoantibody Producing Cells in Neuromyelitis Optica," *Journal of Clinical and Experimental Medicine*, vol. 240:534-535, 2012.
Christensen et al., "Systemic Inflammation in Progressive Multiple Sclerosis Involves Follicular T-Helper, TH17- and Activated B-Cells and Correlates with Progression," *PLoS ONE*, vol. 8:e57820, 2013.
Hosokawa et al., "The Response to Treatment with Interferon beta-1b in Patients with Multiple Sclerosis," *Shinkei Chiryo*, vol. 25:589-595, 2008.
International Search Report (English translation), for PCT Application No. PCT/JP2014/065449, 2 pages (dated Sep. 22, 2014).
Kakuron III, "Section 9 Opticospinal Multiple Sclerosis", *Tahatsusei Kokasho Chiryo Guideline*, vol. 2010, pp. 104-109, 2010.
Miller et al., "Differential Diagnosis of Suspected Multiple Sclerosis: A Consensus Approach," *Multiple Sclerosis*: vol. 14:1157-1174, 2008.
Nakamura et al., "IL-6-dependent Plasmablasts in Pathological Conditions of Relapsing-Remitting Multiple Sclerosis," *Jap. J. Clin. Immunol.*, vol. 36:345, W5-5, 2013.

(56) References Cited

OTHER PUBLICATIONS

Nakamura et al., "Clinical Features of Multiple Sclerosis with High Plasmablast Frequency in Peripheral Blood," Poster Session, 54th Annual Meeting of the Japanese Society of Neurology, Tokyo, Japan, presented Jun. 1, 2013.

Nakamura et al., "Clinical Characteristics of Multiple Sclerosis with High Peripheral Blood Plasmablast Frequency", Meeting Abstract, 54th Annual Meeting of the Japanese Society of Neurology, Tokyo, Japan, published Apr. 30, 2013.

Nakamura et al., "Clinical Features of Multiple Sclerosis with High Plasmablast Frequency in Peripheral Blood." Poster Session, Multiple Sclerosis, Keystone Symposia on Molecular and Cellular Biology, Big Sky, Montana, presented Jan. 14, 2013.

Nakamura et al., "Clinical Features of Multiple Sclerosis with High Plasmablast Frequency in Peripheral Blood," Abstract, Multiple Sclerosis, Keystone Symposia on Molecular and Cellular Biology, Big Sky, Montana published online Dec. 11, 2012.

Nakamura et al., "Clinical Features of Multiple Sclerosis with High Plasmablast Frequency in Peripheral Blood", Abstract for Poster Session, Multiple Sclerosis, Keystone Symposia on Molecular and Cellular Biology, Big Sky, Montana, distributed Jan. 11, 2013.

Shimizu et al., "IFNβ-1b May Severely Exacerbate Japanese Optic-Spinal MS in Neuromyelitis Optica Spectrum," *Neurology*, vol. 75:1423-1427, 2010.

Tintoré et al., Isolated Demyelinating Syndromes: Comparison of Different MR Imaging Criteria to Predict Conversion to Clinically Definite Multiple Sclerosis, *AJNR Am. J. Neuroradiol.*, vol. 21:702-706, 2000.

Waubant et al., "Clinical Characteristics of Responders to Interferon Therapy for Relapsing MS," *Neurology*, vol. 61:184-189, 2003.

Bartelds et al., "Clinical response to adalimumab: relationship to anti-adalimumab antibodies and serum adalimumab concentrations in rheumatoid arthritis," *Ann. Rheum. Dis.*, vol. 66(7):921-926, 2007.

Bender et al., "Immunogenicity, efficacy and adverse events of adalimumab in RA patients," *Rheumatol. Int.*, vol. 27(3):269-274, 2006.

Chihara and Yamamura, "Autoantibody producing cells in neuromyelitis optica," *J. Clin. Exper. Med.*, vol. 240:534-535, 2012.

Chihara et al., "Interleukin 6 signaling promotes anti-aquaporin 4 autoantibody production from plasmablasts in neuromyelitis optica," *Proc. Natl. Acad. Sci. USA*, vol. 108:3701-3706, 2011.

Chirino et al., "Minimizing the immunogenicity of protein therapeutics," *Drug Discov. Today*, vol. 9(2):82-90, 2004.

Choy E., "Inhibiting Interleukin-6 in Rheumatoid Arthritis," *Curr. Rheumatol. Rep.*, vol. 10(5):413-417, 2008.

Cocco et al., "In Vitro Generation of Long-lived Human Plasma Cells," *J. Immunol.*, vol. 189(12):5773-5785, 2012.

Dillon et al., "Structural and Functional Characterization of Disulfide Isoforms of the Human IgG2 Subclass," *J. Biol. Chem.*, vol. 283(23):16206-16215, 2008.

Ewert et al., "Stability improvement of antibodies for extracellular and intracellular applications: CDR grafting to stable frameworks and structure-based framework engineering," *Methods*, vol. 34(2):184-199, 2004.

Gessner et al., "The IgG Fc receptor family," *Ann. Hematol.*, vol. 76(6):231-248, 1998.

Ghetie et al., "Increasing the serum persistence of an IgG fragment by random mutagenesis," *Nat. Biotechnol.*, vol. 15(7):637-640, 1997.

Guerne PA et al., "Synovium as a Source of Interleukin 6 in Vitro," *J. Clin. Invest.*, vol. 83(2):585-592, 1989.

Besada et al., "Potential patient benefit of a subcutaneous formulation of tocilizumab for the treatment of rheumatoid arthritis: a critical review," *Patient Prefer Adherence* 8:1051-1059, 2014.

Huizinga et al., "Sarilumab, a fully human monoclonal antibody against IL-6Ra in patients with rheumatoid arthritis and an inadequate response to methotrexate: efficacy and safety results from the randomised SARIL-RA-MOBILITY Part A trial," *Ann Rheum Dis* 73:1626-1634, 2014.

Kayahara et al., "Neural Invasion and Lymph node Metastasis in the Head of the Pancreas Carcinoma," *The Japanese Journal of the Gastroenterological Surgery* 24(3):813-817, 1991 (with English Abstract).

Nakamura et al., "Cancer prevention by NK 4 to act as an inhibitor of tumor invasion, metastasis and angiogenesis," The Basics and Clinical Aspects of Angiogenesis—[II] Angiogenesis and Tumors, 8. Invasion/Metastasis/Tumor Suppression of Angiogenesis-Inhibitory Factor AK 4, pp. 57-66, Japanese Association of Medical Sciences, 2002.

Yan et al., "Abdominal discomfort and pain," *Theory and Practice of Oncology*, Shandong Science and Technology Press, Jul. 2006.

Zijun et al., "Tissue Infiltration," *Tumor Metastasis*, Shanxi Science and Technology Press, Feb. 2007, pp. 15-16.

ACTEMRA Prescribing Information (1 page).

Ando et al., "Tocilizumab, a Proposed Therapy for the Cachexia of Interleukin6-Expressing Lung Cancer," *PLoS ONE*, vol. 9:e102436, 2014.

Costa et al., "Efficacy of Tocilizumab in a Patient with Refractory Psoriatic Arthritis," *Clin. Rheumatol.*, vol. 33:1355-1357, 2014.

Furuya et al., "Interleukin-6 as a Potential Therapeutic Target for Pulmonary Arterial Hypertension," *Int. J. Rheumatol.*, vol. 2010, 9 pp., 2010.

Hashizume et al., "Tocilizumab, a Humanized Anti-Interleukin-6 Receptor Antibody, Improved Anemia in Monkey Arthritis by Suppressing IL-6-Induced Hepcidin Production," *Rheumatol. Int.*, vol. 30:917-923, 2010.

Honda et al., "Marginal Zone B Cells Exacerbate Endotoxic Shock via Interleukin-6 Secretion Induced by Fcα/μR-coupled TLR4 Signalling," *Nat. Comm.*, vol. 7:11498, 2016.

Iijima et al., "Tocilizumab Improves Systemic Rheumatoid Vasculitis with Necrotizing Crescentic Glomerulonephritis," *Mod. Rheumatol.*, vol. 25:138-142, 2015.

Kishimoto, "Interleukin-6 and its Receptor in Autoimmunity," *J. Autoimmun..*, vol. 5:123-132, 1992.

Kondo et al., "A Case of Overlap Syndrome Successfully Treated with Tocilizumab: A Hopeful Treatment Strategy for Refractory Dermatomyositis?" *Rheumatol.*, vol. 53:1907-1908, 2014.

Mihara et al., "Anti-Interleukin 6 Receptor Antibody Inhibits Murine AA-Amyloidosis," *J. Rheumatol.*, vol. 31: 1132-1138, 2004.

Mori et al., "Novel Models of Cancer-Related Anemia in Mice Inoculated with IL-6 Producing Tumor Cells," *Biomed. Res.*, vol. 30:47-51, 2009.

Motozawa et al., "Unique Circumferential Peripheral Keratitis in Relapsing Polychondritis," *Medicine*, vol. 96:41, 4 pp., 2017.

Narazaki et al., "Therapeutic Effect of Tocilizumab on Two Patients with Polymyositis," *Rheumatol.*, vol. 50:1344-1346, 2011.

Serada et al., "IL-6 Blockade Inhibits the Induction of Myelin Antigen-Specific Th17 Cells and Th1 Cells in Experimental Autoimmune Encephalomyelitis," *Proc. Nat. Acad. Sci. USA.*, vol. 105:9041-9046, 2008.

Shima et al., "Tocilizumab, a Humanized Anti-Interleukin-6 Receptor Antibody, Ameliorated Clinical Symptoms and MRI Findings of a Patient with Ankylosing Spondylitis," *Mod. Rheumatol.*, vol. 21:436-439, 2011.

Shimizu et al., "Successful Treatment with Tocilizumab for Refractory Scleritis Associated with Relapsing Polychondritis," *Scand. J. Rheumatol.*, vol. 46:418-419, 2017.

Silpa-Archa et al., "Outcome of Tocilizumab Treatment in Refractory Ocular Inflammatory Diseases," *Acta Ophthalmol.*, vol. 94:e400-e406, 2016.

Suzuki et al., "Anti-Murine IL-6 Receptor Antibody Inhibits IL-6 Effects in Vivo," *Immunol. Lett.*, vol. 30:17-22, 1991.

Office Action dated Feb. 26, 2019, in connection with U.S. Appl. No. 15/575,027 (7 pages).

Okiyama et al., "Therapeutic Effects of Interleukin-6 Blockade in a Murine Model of Polymyositis That Does Not Require Interleukin-17A," *Arthritis Rheum* 60(8):2505-2512, 2009.

Jones et al., "Identification and removal of a promiscuous CD4+ T cell epitope from the C1 domain of factor VIII," *J. Thromb. Haemost.*, vol. 3(5):991-1000, 2005.

(56) References Cited

OTHER PUBLICATIONS

Anonymous, "Interleukin 6," Wikipedia, Feb. 22, 2019, XP055598802, https://protect-us.mimecast.com/s/6UxpCmZ28nsApl8JuGhTki?domain=en.wikipedia.org (retrieved on Jun. 24, 2019; 20 pages).

Armour et al., "Recombinant Human IgG Molecules Lacking Fcγ Receptor I Binding and Monocyte Triggering Activities," *Eur J Immunol.*, vol. 29:2613-2624, 1999.

Brown et al., Tolerance to Single, but Not Multiple, Amino Acid Replacements in Antibody $V_H$ CDR2, *J Immunol.*, vol. 156:3285-3291, 1996.

Chau et al., "HuM291(NUVION), A Humanized Fc Receptor-Nonbinding Antibody Against CD3, Anergizes Peripheral Blood T Cells as Partial Agonist of the T Cell Receptor," *Transplantation*, vol. 71:941-950, 2001.

Chien et al., "Significant Structural and Functional Change of an Antigen-Binding Site by a Distant Amino Acid Substitution: Proposal of a Structural Mechanism," *Proc. Natl. Acad. Sci. USA*, vol. 86:5532-5536, 1989.

Chu et al., "Accumulation of Succinimide in a Recombinant Monoclonal Antibody in Mildly Acidic Buffers Under Elevated Temperatures," *Pharm. Res.*, vol. 24:1145-1156, 2007.

Cole et al., "Human IgG2 Variants of Chimeric Anti-CD3 are Nonmitogenic to T Cells," *J. Immunol.*, vol. 159:3613-3621, 1997.

Cordoba et al., "Non-Enzymatic Hinge Region Fragmentation of Antibodies in Solution," *J. Chromatogr. B*, vol. 818:115-121, 2005.

Damschroder et al., "Framework Shuffling of Antibodies to Reduce Immunogenicity and Manipulate Functional and Biophysical Properties," *Mol. Immunol.*, vol. 44:3049-3060, 2007.

Davies et al., "Affinity Improvement of Single Antibody VH Domains: Residues in all Three Hypervariable Regions Affect Antigen Binding," *Immunotech.*, vol. 2:169-179, 1996.

De Pascalis et al., "Grafting of "Abbreviated" Complementarity-Determining Regions Containing Specificity-Determining Residues Essential for Ligand Contact to Engineer a Less Immunogenic Humanized Monoclonal Antibody," *J. Immunol.*, vol. 169:3076-3084, 2002.

Guyre et al., "Increased Potency of Fc-Receptor-Targeted Antigens," *Cancer Immunol. Immunother.*, vol. 45:146-148, 1997.

Holt et al., "Domain Antibodies: Proteins for Therapy," *Trends Biotechnol.*, vol. 21:484-490, 2003.

Maynard et al., "Antibody Engineering," *Annu. Rev. Biomed. Eng.*, vol. 2:339-376, 2000.

Ohno et al., "Antigen-Binding Specificities of Antibodies are Primarily Determined by Seven Residues of $V_H$," *Proc. Natl. Acad. Sci. USA*, vol. 82:2945-2949, 1985.

Pini et al., "Design and Use of a Phage Display Library," *J. Biol. Chem.*, vol. 273:21769-21776, 1998.

Reddy et al., "Elimination of Fc Receptor-Dependent Effector Functions of a Modified IgG4 Monoclonal Antibody to Human CD4," *J. Immunol.*, vol. 164:1925-1933, 2000.

Takkinen et al., "Affinity and Specificity Maturation by CDR Walking," *Antibody Engineering*, Springer Lab Manuals 2001, pp. 540-545.

Tan et al., "Engineering the Isoelectric Point of a Renal Cell Carcinoma Targeting Antibody Greatly Enhances scFv Solubility," *Immunotech.*, vol. 4:107-114, 1998.

Teeling et al., "The Biological Activity of Human CD20 Monoclonal Antibodies is Linked to Unique Epitopes on CD20," *J. Immunol.*, vol. 177:362-371, 2006.

Vajdos et al., "Comprehensive Functional Maps of the Antigen-binding Site of an Anti-ErbB2 Antibody Obtained with Shotgun Scanning Mutagenesis," *J. Mol. Biol.*, vol. 320:415-428, 2002.

Wu et al., "Humanization of a Murine Monoclonal Antibody by Simultaneous Optimization of Framework and CDR Residues," *J. Mol. Biol.*, vol. 294:151-162, 1999.

Office Action issued in U.S. Appl. No. 15/575,027 dated Oct. 25, 2019 (14 pages).

Chugai NMO Clinical Trial Webinar, Sakura Star Study, dated Dec. 12, 2014, downloaded on Sep. 5, 2019 from https://s3.amazonaws.com/gjcf-wp-uploads/wp-content/uploads/2016/05/16162202/12_12_14_Chugai_Webinar_PPT_Complete_Deck_FINAL.pdf,18 pages.

Chugai Pharmaceutical, A phase I, multiple-dose study of SA237, Study JapicCTI-No. 121786; submitted to Clinicaltrials.jp on Jan. 31, 2014; downloaded from clinicaltrials.jp archive on Sep. 5, 2019 as https://www.clinicaltrials.jp/cti-user/trial/Show.jsp, 5 pages.

Chugai Pharmaceutical, A phase I, multiple-dose study of SA237, Study JapicCTI-No. 121786; submitted to Clinicaltrials.jp on Mar. 19, 2012; downloaded from clinicaltrials.jp archive on Sep. 5, 2019 as https://www.clinicaltrials.jp/cti-user/trial/Show.jsp, 5 pages.

Chugai Pharmaceutical, A phase I, multiple-dose study of SA237, Study JapicCTI-No. 121786; submitted to Clinicaltrials.jp on Jun. 19, 2012; downloaded from clinicaltrials.jp archive on Sep. 5, 2019 as https://www.clinicaltrials.jp/cti-user/trial/Show.jsp, 5 pages.

Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 1; submitted to ClinicalTrials.gov on Jan. 6, 2014; downloaded from ClinicalTrials.gov archive on Sep. 4, 2019 as https://clinicaltrials.gov/ct2/history/NCT02028884?V_1=View#StudyPageTop, 6 pages.

Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 2; submitted to ClinicalTrials.gov on Feb. 25, 2014; downloaded from ClinicalTrials.gov archive on Sep. 4, 2019 as https://clinicaltrials.gov/ct2/history/NCT02028884?V_2=View#StudyPageTop, 6 pages.

Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 3; submitted to ClinicalTrials.gov on Sep. 4, 2015; downloaded from ClinicalTrials.gov archive on Sep. 4, 2019 as https://clinicaltrials.gov/ct2/history/NCT02028884?V_3=View#StudyPageTop, 6 pages.

Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 4; submitted to ClinicalTrials.gov on Dec. 8, 2015; downloaded from.ClinicalTrials.gov archive on Sep. 4, 2019 as https://clinicaltrials.gov/ct2/history/NCT02028884?V_4=View#StudyPageTop, 6 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 1; submitted to ClinicalTrials.gov on Feb. 25, 2014; downloaded from ClinicalTrials.gov archive on Sep. 4, 2019 as https://clinicaltrials.gov/ct2/history/NCT02073279?V_1=View#StudyPageTop, 6 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 10; submitted to ClinicalTrials.gov on Jul. 7, 2015; downloaded from ClinicalTrials.gov archive on Sep. 5, 2019 as https://clinicaltrials.gov/ct2/history/NCT02073279?V_10=View#StudyPageTop, 9 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 11; submitted to ClinicalTrials.gov on Aug. 3, 2015; downloaded from ClinicalTrials.gov archive on Sep. 5, 2019 as https://clinicaltrials.gov/ct2/history/NCT02073279?V_11=View#StudyPageTop, 10 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 12; submitted to ClinicalTrials.gov on Sep. 3, 2015; downloaded from ClinicalTrials.gov archive on Sep. 5, 2019 as https://clinicaltrials.gov/ct2/history/NCT02073279?V_12=View#StudyPageTop, 10 pages.

(56) References Cited

OTHER PUBLICATIONS

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 13; submitted to ClinicalTrials.gov on Oct. 5, 2015; downloaded from ClinicalTrials.gov archive on Sep. 5, 2019 as https://clinicaltrials.gov/ct2/history/NCT02073279?V_13=View#StudyPageTop, 10 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 14; submitted to ClinicalTrials.gov on Dec. 8, 2015; downloaded from ClinicalTrials.gov archive on Sep. 5, 2019 as https://clinicaltrials.gov/ct2/history/NCT02073279?V_14=View#StudyPageTop, 10 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 2; submitted to ClinicalTrials.gov on Jul. 22, 2014; downloaded from ClinicalTrials.gov archive on Sep. 5, 2019 as https://clinicaltrials.gov/ct2/history/NCT02073279?V_2=View#StudyPageTop, 6 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 3; submitted to ClinicalTrials.gov on Dec. 15, 2014; downloaded from ClinicalTrials.gov archive on Sep. 5, 2019 as https://clinicaltrials.gov/ct2/history/NCT02073279?V_3=View#StudyPageTop, 7 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 4; submitted to ClinicalTrials.gov on Feb. 5, 2015; downloaded from ClinicalTrials.gov archive on Sep. 5, 2019 as https://clinicaltrials.gov/ct2/history/NCT02073279?V_4=View#StudyPageTop, 8 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 5; submitted to ClinicalTrials.gov on Feb. 6, 2015; downloaded from ClinicalTrials.gov archive on Sep. 5, 2019 as https://clinicaltrials.gov/ct2/history/NCT02073279?V_5=View#StudyPageTop, 8 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 6; submitted to ClinicalTrials.gov on Mar. 4, 2015; downloaded from ClinicalTrials.gov archive on Sep. 5, 2019 as https://clinicaltrials.gov/ct2/history/NCT02073279?V_6=View#StudyPageTop, 9 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 7; submitted to ClinicalTrials.gov on Apr. 1, 2015; downloaded from ClinicalTrials.gov archive on Sep. 5, 2019 as https://clinicaltrials.gov/ct2/history/NCT02073279?V_7=View#StudyPageTop, 9 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 8; submitted to ClinicalTrials.gov on May 7, 2015; downloaded from ClinicalTrials.gov archive on Sep. 5, 2019 as https://clinicaltrials.gov/ct2/history/NCT02073279?V_8=View#StudyPageTop, 9 pages.

Chugai Pharmaceutical, Efficacy and Safety Study of Satralizumab SA237) as Monotherapy to Treat Participants With Neuromyelitis Optica (NMO) and Neuromyelitis Optica Spectrum Disorder (NMOSD), Study NCT02073279, version 9; submitted to ClinicalTrials.gov on Jun. 5, 2015; downloaded from ClinicalTrials.gov archive on Sep. 5, 2019 as https://clinicaltrials.gov/ct2/history/NCT02073279?V_9=View#StudyPageTop, 9 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Germany; submitted to clinicaltrialsregister.eu on Dec. 20, 2013; downloaded from clinicaltrialsregister.eu archive on Sep. 5, 2019 ashttps://www.clinicaltrialsregister.eu/ctr-search/trial/2013-003752-21/DE, 7 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Hungary; submitted to clinicaltrialsregister.eu on Feb. 25, 2015; downloaded from clinicaltrialsregister.eu archive on Sep. 5, 2019 ashttps://www.clinicaltrialsregister.eu/ctr-search/trial/2013-003752-21/HU, 6 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Italy; submitted to clinicaltrialsregister.eu on Feb. 6, 2014; downloaded from clinicaltrialsregister.eu archive on Sep. 5, 2019 ashttps://www.clinicaltrialsregister.eu/ctr-search/trial/2013-003752-21/IT, 5 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Poland; submitted to clinicaltrialsregister.eu on Jul. 4, 2014; downloaded from clinicaltrialsregister.eu archive on Sep. 5, 2019 ashttps://www.clinicaltrialsregister.eu/ctr-search/trial/2013-003752-21/GB, 7 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Spain; submitted to clinicaltrialsregister.eu on Mar. 11, 2015; downloaded from clinicaltrialsregister.eu archive on Sep. 5, 2019 ashttps://www.clinicaltrialsregister.eu/ctr-search/trial/2013-003752-21/ES, 7 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in the United Kingdom; submitted to clinicaltrialsregister.eu on Oct. 15, 2013; downloaded from clinicaltrialsregister.eu archive on Sep. 5, 2019 ashttps://www.clinicaltrialsregister.eu/ctr-search/trial/2013-003752-21/GB, 6 pages.

F. Hoffmann-La Roche Ltd., A Multicenter, Randomized, Double-blind, Placebo-controlled, Phase 3 Study to Evaluate the Efficacy and Safety of Satralizumab (SA237) as Monotherapy in Patients With Neuromyelitis Optica (NMO) and Neuromyelitis Optica Spectrum Disorder(NMOSD), Study EudraCT 2015-005431-41 in Croatia; submitted to clinicaltrialsregister.eu on Dec. 15, 2016; downloaded from clinicaltrialsregister.eu archive on Sep. 5, 2019 ashttps://www.clinicaltrialsregister.eu/ctr-search/trial/2015-005431-41/HR, 6 pages.

F. Hoffmann-La Roche Ltd., A Multicenter, Randomized, Double-blind, Placebo-controlled, Phase 3 Study to Evaluate the Efficacy and Safety of Satralizumab (SA237) as Monotherapy in Patients With Neuromyelitis Optica (NMO) and Neuromyelitis Optica Spectrum Disorder(NMOSD), Study EudraCT 2015-005431-41 in Poland; submitted to clinicaltrialsregister.eu on Apr. 7, 2016; downloaded from clinicaltrialsregister.eu archive on Sep. 5, 2019 ashttps://www.clinicaltrialsregister.eu/ctr-search/trial/2015-005431-41/PL, 6 pages.

Hanes et al., "Picomolar affinity antibodies from a fully synthetic naive library selected and evolved by ribosome display," *Nat. Biotechnol.*, vol. 18(12):1287-1292, 2000.

(56) References Cited

OTHER PUBLICATIONS

Hinton et al., "An Engineered Human IgG1 Antibody with Longer Serum Half-Life," *J. Immunol.*, vol. 176(1):346-356, 2006.
Hirano et al., "Excessive production of interleukin 6/B cell stimulatory factor-2 in rheumatoid arthritis," *Eur. J. Immunol.*, vol. 18(11):1797-1801, 1988.
Houssiau FA et al., "Interleukin-6 in Synovial Fluid and Serum of Patients with Rheumatoid Arthritis and Other Inflammatory Arthritides," *Arthritis Rheum.*, vol.31(6):784-788, 1988.
Houzen et al., "Increased prevalence, incidence, and female predominance of multiple sclerosis in northern Japan," *J. Neurol. Sci.*, vol. 323:117-122, 2012.
Hwang et al., "Use of human germline genes in a CDR homology-based approach to antibody humanization," *Methods*, vol. 36(1):35-42, 2005.
Ito et al., "The His-probe method: effects of histidine residues introduced into the complementarity-determining regions of antibodies on antigen-antibody interactions at different pH values," *FEBS*, vol. 309(1):85-88, 1992.
Jego et al., "Interleukin-6 is a growth factor for nonmalignant human plasmablasts," *Blood*, vol. 97(6):1817-1822, 2001.
Johnson et al., "Cation exchange-HPLC and mass spectrometry reveal C-terminal amidation of an IgG1 heavy chain," *Anal. Biochem.*, vol. 360(1):75-83, 2006.
Jones et al., "Identification and removal of a promiscuous CD4+ T cell epitope from the C1 domain of factor VIII," *J. Thromb. Haemost.*, vol. 3(5):991-1000, 2005.
Jourdan et al., "An in vitro model of differentiation of memory B cells into plasmablasts and plasma cells including detailed phenotypic and molecular characterization," *Blood*, vol. 114(25):5173-5181, 2009.
Kim et al., "Antibody Engineering for the Development of Therapeutic Antibodies," *Mol. Cells*, vol. 20(1):17-29, 2005.
Kishimoto T., "The Biology of Interleukin-6," *Blood*, vol. 74(1):1-10, 1989.
Kotake S. et al., "Interleukin-6 and Soluble Interleukin-6 Receptors in the Synovial Fluids from Rheumatoid Arthritis Patients Are Responsible for Osteoclast-like Cell Formation," *J. Bone Miner. Res.*, vol. 11(1):88-95, 1996.
Krieckaert et al., "Immunogenicity of biologic therapies—we need tolerance," *Nat. Rev. Rheumatol.*, vol. 6(10):558-559, 2010.
Lucchinetti et al, "Heterogeneity of Multiple Sclerosis Lesions: Implications for the Pathogenesis of Demyelination," *Ann. Neurol.*, vol. 47:707-717, 2000.
Maccallum et al., "Antibody-antigen Interactions: Contact Analysis and Binding Site Topography," *J. Mol. Biol.*, vol. 262(5):732-745, 1996.
Madhok R. et al., "Serum interleukin 6 levels in rheumatoid arthritis: correlations with clinical and laboratory indices of disease activity," *Ann. Rheum. Dis.*, vol. 52(3):232-234, 1993.
Maini et al., "Double-Blind Randomized Controlled Clinical Trial of the Interleukin-6 Receptor Antagonist, Tocilizumab, in European Patients with Rheumatoid Arthritis who had an Incomplete Response to Methotrexate,", *Arthritis Rheum.*, vol. 54(9):2817-29, 2006.
Matsumoto et al., "Interleukin-10-Producing Plasmablasts Exert Regulatory Function in Autoimmune Inflammation," *Immunity*, vol. 41(6):1040-1051, 2014.
Mihara et al., "Tocilizumab inhibits signal transduction mediated by both mIL-6R and sIL-6R, but not by the receptors of other members of IL-6 cytokine family," *Int. Immunopharmacol.*, vol. 5(12):1731-1740, 2005.
Miller et al., "Differential diagnosis of suspected multiple sclerosis: a consensus approach," *Mult. Scler.*, vol. 14:1157-1174, 2008.
Nishimoto et al., "Clinical Studies in Patients With Castleman's Disease, Crohn's Disease, and Rheumatoid Arthritis in Japan," *Clin. Rev. Allergy Immunol.*, vol. 28(3):221-230, 2005.
Nishimoto et al., "Interleukin-6: from bench to bedside," *Nat. Clin. Pract. Rheumatol.*, vol. 2(11):619-626, 2006.
Non-Final Office Action dated Feb. 23, 2018, from U.S. Appl. No. 15/263,617 (9 pages).

Ohsugi, "Success Story of Pre-market Approved Pipeline," *Pharm. Stage.*, vol. 7(5):1-8, 2007.
Onda et al., "Lowering the Isoelectric Point of the Fv Portion of Recombinant Immunotoxins Leads to Decreased Nonspecific Animal Toxicity without Affecting Antitumor Activity," *Cancer Res.*, vol. 61(13):5070-5077, 2001.
Padlan et al., "Structure of an antibody-antigen complex: Crystal structure of the HyHEL-10 Fab-lysozyme complex," *Proc. Natl. Acad. Sci. USA*, vol. 86(15):5938-5942, 1989.
Pavlou et al., "The therapeutic antibodies market to 2008," *Eur. J. Pharm. Biopharm*, vol. 59(3):389-396, 2005.
Rajpal et al., "A general method for greatly improving the affinity of antibodies by using combinatorial libraries," *Proc. Natl. Acad. Sci. USA*, 102(24):8466-8471, 2005.
Reichert et al., "Monoclonal antibody successes in the clinic," *Nat. Biotechnol.*, vol. 23(9):1073-1078, 2005.
Roitt et al., Immunology, M., Mir, 2000, p. 110. (in Russian with English translation).
Rothe et al., "Ribosome display for improved biotherapeutic molecules," *Expert Opin. Biol. Ther.*, vol. 6(2):177-187, 2006.
Rudikoff et al., "Single amino acid substitution altering antigen-binding specificity," *Proc. Natl. Acad. Sci. U.S.A.*, vol. 79(6):1979-1983, 1982.
Sack, U. et al., "Interleukin-6 in synovial fluid is closely associated with chronic synovitis in rheumatoid arthritis," *Rheumatol. Int.*, vol. 13(2):45-51, 1993.
Salfeld, "Isotype selection in antibody engineering," *Nat. Biotechnol.*, vol. 25(12):1369-1372, 2007.
Sato et al., "Reshaping a Human Antibody to Inhibit the Interleukin 6-dependent Tumor Cell Growth," *Cancer Res.*, vol. 53(4):851-856, 1993.
Sebba et al., "Tocilizumab: The first interleukin-6-receptor inhibitor," *Am. J. Health Syst. Pharm.*, vol. 65(15):1413-1418, 2008.
Shire et al., "Challenges in the Development of High Protein Concentration Formulations," *J. Pharm. Sci.*, vol. 93(6):1390-1402, 2004.
Srivastava et al., "Potassium Channel KIR4.1 as an Immune Target in Multiple Sclerosis," *N. Engl. J. Med.*, vol. 367:115-123, 2012.
Strand et al., "Biologic therapies in rheumatology: lessons learned, future directions," *Nat. Rev. Drug Discov*, vol. 6(1):75-92, 2007.
Tamura et al., "Soluble interleukin-6 receptor triggers osteoclast formation by interleukin 6," *Proc. Natl. Acad. Sci. U.S.A.*, vol. 90(24):11924-11928, 1993.
Tintoré et al., "Isolated Demyelinating Syndromes: Comparison of Different MR Imaging Criteria to Predict Conversion to Clinically Definite Multiple Sclerosis," *Am. J. Neuroradiol.*, vol. 21:702-706, 2000.
Van Walle et al., "Immunogenicity screening in protein drug development," *Expert Opin. Biol. Ther.*, vol. 7(3):405-418, 2007.
Wu et al., "Development of Motavizumab, an Ultra-potent Antibody for the Prevention of Respiratory Syncytial Virus Infection in the Upper and Lower Respiratory Tract," *J. Mol. Biol.*, vol. 368(3):652-665, 2007.
Yokota et al., "Clinical Study of Tocilizumab in Children With Systemic-Onset Juvenile Idiopathic Arthritis," *Clin. Rev. Allergy Immunol.*, vol. 28(3):231-238, 2005.
U.S. Appl. No. 15/575,027, filed Nov. 17, 2017.
U.S. Appl. No. 12/860,112, filed Aug. 20, 2010.
U.S. Appl. No. 13/959,489, filed Aug. 5, 2013.
U.S. Appl. No. 12/680,087, filed Jan. 3, 2011.
U.S. Appl. No. 13/524,528, filed Jun. 15, 2012.
U.S. Appl. No. 14/520,423, filed Oct. 22, 2014.
U.S. Appl. No. 12/090,061, filed Mar. 6, 2009.
U.S. Appl. No. 12/085,065, filed Jun. 1, 2009.
U.S. Appl. No. 12/090,676, filed Feb. 25, 2009.
U.S. Appl. No. 12/094,644, filed Feb. 27, 2009.
U.S. Appl. No. 12/161,733, filed Mar. 9, 2009.
U.S. Appl. No. 12/296,193, filed Apr. 15, 2009.
U.S. Appl. No. 12/524,041, filed Sep. 18, 2009.
U.S. Appl. No. 12/996,162, filed Mar. 7, 2011.
U.S. Appl. No. 13/387,292, filed Apr. 3, 2012.
U.S. Appl. No. 13/700,355, filed Apr. 2, 2013.
Araki et al., "Latest Treatments and Prospects for Neuromyelitis Optica," *The Medical Frontline*, vol. 71:1159-1167, 2016.
Dall'Acqua et al., "Properties of Human IgG1s Engineered for Enhanced Binding to the Neonatal Fc Receptor (FcRn)," *J. Biol. Chem.*, vol. 281:23514-23524, 2006.

(56) References Cited

OTHER PUBLICATIONS

Hisanaga et al., "Neuro-Behçet Disease and Neuro-Sweet Disease," *Clin. Neurol.*, vol. 52:1234-1236, 2012.

Ishikawa et al., "DNA Microarray Analysis of SLE Related Genes that Respond to IL-6 Blockade with Tocilizumab, an Anti-IL-6 Receptor Monoclonal Antibody," *Ann. Rheum. Dis.*, vol. 65:474, 2006.

Jacob et al., "Detrimental Role of Granulocyte-Colony Stimulating Factor in Neuromyelitis Optica: Clinical Case and Histological Evidence," *Mult. Scler. J.*, vol. 18:1801-1803, 2012.

Nishimoto et al., "Expressions of Immune Response Related Genes were Normalised after Tocilizumab Treatment in Rheumatoid Arthritis (RA) Patients," *Ann. Rheum. Dis.*, vol. 71:380, 2013.

Pérez-Sánchez et al., "Diagnostic Potential of NETosis-Derived Products for Disease Activity, Atherosclerosis and Therapeutic Effectiveness in Rheumatoid Arthritis Patients," *J. Autoimmun.*, vol. 82:31-40, 2017.

Ruiz-Limón et al., "Tocilizumab Improves the Proatherothrombotic Profile of Rheumatoid Arthritis Patients Modulating Endothelial Dysfunction, NETosis, and Inflammation," *Transl. Res.*, vol. 183:87-103, 2017.

Saadoun et al., "Neutrophil Protease Inhibition Reduces Neuromyelitis Optica-Immunoglobulin G-Induced Damage in Mouse Brain," *Ann. Neurol.*, vol. 71:323-333, 2012.

Tanaka et al., "Therapeutic Targeting of the Interleukin-6 Receptor," *Annu. Rev. Pharmacol. Toxicol.* vol. 52:199-219, 2012.

Yamamura et al., "Anti-IL-6 Receptor Therapy for Neuromyelitis Optica," *Neurol. Thera.*, vol. 33:S120, 2016.

Yamamura, "Anti-IL-6 Receptor Antibody Therapy against Neuromyelitis Optica (NMO)," *The 34th Annual Meeting of the Japanese Society of Neurological Therapeutics*, Nov. 4, 2016.

Yamamura, "Treatment Failures in NMO are due to Specific Immunologic Mechanisms," *9th Annual International Roundtable Conference on NMO*, Mar. 13, 2017.

* cited by examiner

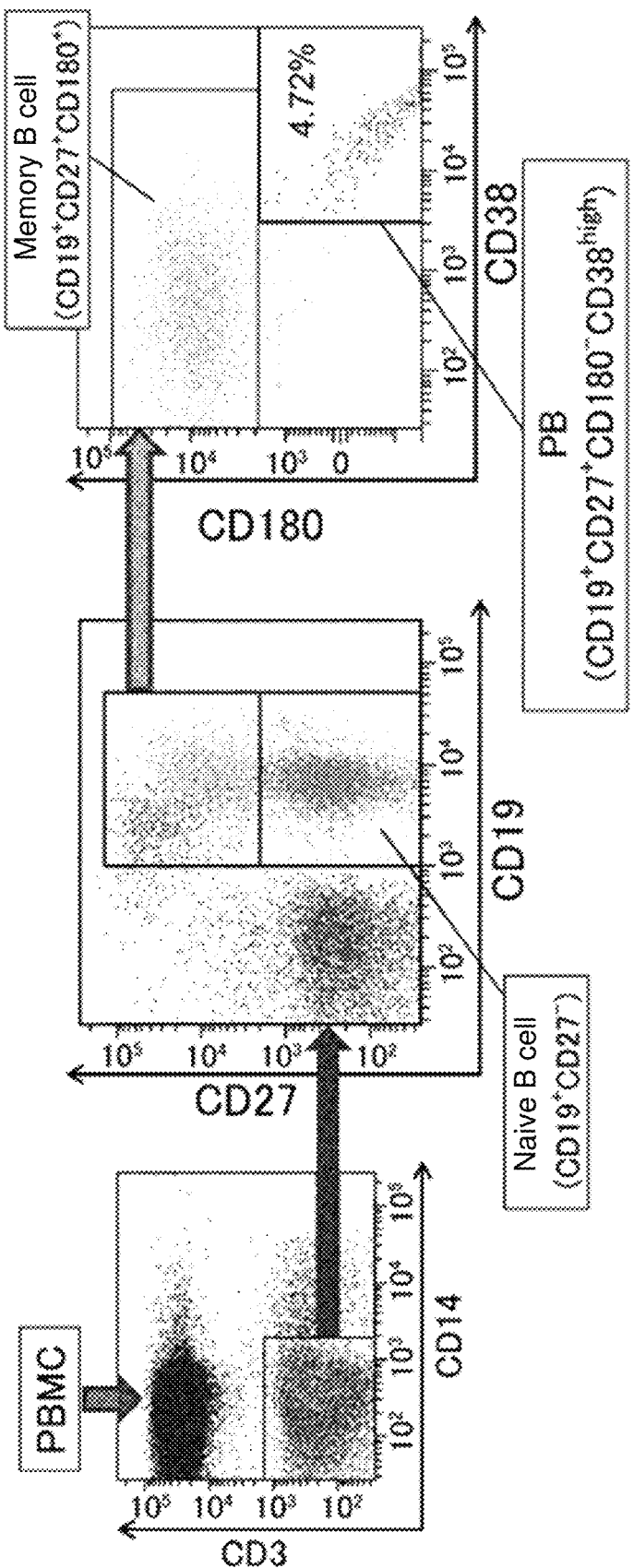

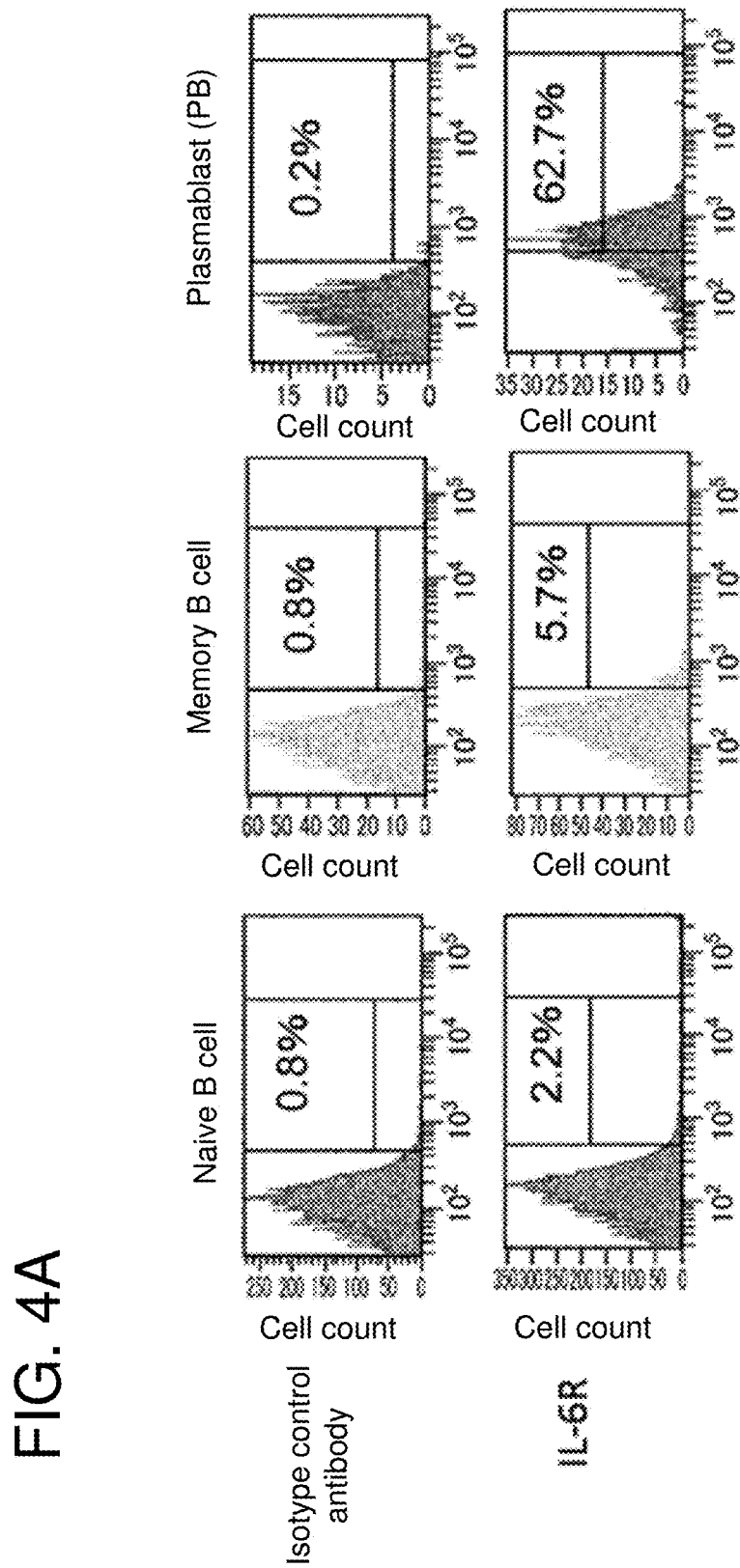

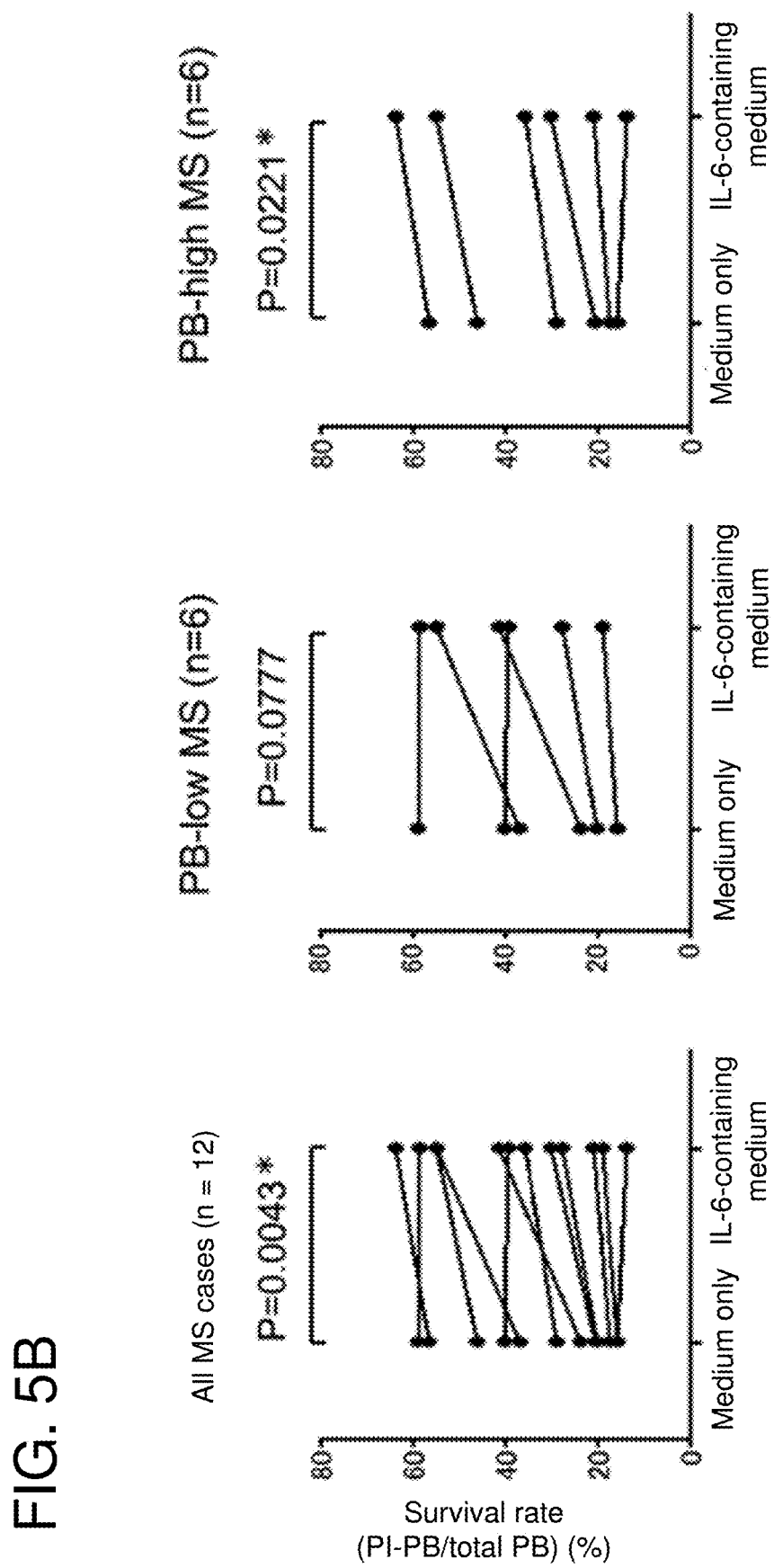

METHOD FOR PREDICTING POST-THERAPY PROGNOSIS OF RELAPSING-REMITTING MULTIPLE SCLEROSIS (RRMS) PATIENT, AND METHOD FOR DETERMINING APPLICABILITY OF NOVEL THERAPY

CROSS REFERENCE TO RELATED APPLICATIONS

This is the U.S. National Stage of International Application No. PCT/JP2014/065449, filed Jun. 11, 2014, which claims the benefit of Japan Patent Application No. 2013-122845, filed Jun. 11, 2013.

TECHNICAL FIELD

The present invention relates to a method for predicting prognosis for the treatment of a relapsing-remitting multiple sclerosis (RRMS) patient with interferon beta (IFN-β) by using a plasmablast (PB) as an index. The present invention also relates to a method for confirming suitability for the treatment of RRMS with an IL-6 inhibitor by using PB as an index. The present invention further relates to a therapeutic agent for RRMS, comprising an IL-6 inhibitor.

BACKGROUND ART

Multiple sclerosis (MS) is considered as an autoimmune disease of the central nervous system. This disease manifests diverse neurological symptoms such as motor paralysis, sensory impairment, higher brain dysfunction, visual loss, and dysuria by infiltrating autoreactive lymphocytes (mainly, T cells or B cells) into the brain, the spinal cord, or the optic nerve and causing inflammations targeting perineural myelin proteins. Approximately a million people are presumed to suffer from this disease worldwide. Particularly, in Western countries, MS is highly prevalent and is known as a typical neurological disease for young adults. Although the disease had been thought to be less common in Asian countries, abrupt increase in its prevalence has been reported in Japan in recent years (Non Patent Literature 1). This strongly suggests the involvement of not only genetic factors but environmental factors in the occurrence of MS, while MS disadvantageously results in the destruction of family life or social life such as occupations due to neurological symptoms remaining as sequelae. The great majority of MS patients have transient and repetitive inflammations at various sites of the central nervous system. As each inflammation occurs, neurological symptoms are manifested in response to the inflammation site. This clinical event is called "relapse", and the course of recurrence is referred to as "relapsing-remitting (RR)". Relapsing-remitting MS (RRMS) exhibits reduction in activities of daily living (ADL) because sequelae accumulate with each relapse. When the duration of RRMS is long, most people with RRMS move on to secondary progressive (SP) MS in which neurological symptoms gradually progress without relapses. At this stage, the great majority of cases already have moderate fixed neurological disability. Thus, treatment from an earlier stage of RRMS seems to be important.

Recombinant interferon beta (IFN-β) has been used as the first line therapy to prevent relapses of patients with RRMS, and is reportedly effective for suppressing the relapses and also effective for suppressing progression in the degree of damage. In Japan, Avonex® (interferon beta-la) and Betaferon® (interferon beta-1b) are used. However, the continuous administration often becomes difficult due to the manifestation of a serious adverse reaction (interstitial pneumonia, autoimmune hepatitis, thyroid dysfunction, skin ulcer, psychological symptoms such as depression, leukopenia, etc.) or the aggravation of an immune disorder, if latent, centering on an autoimmune disorder (collagen disease, thyroiditis, etc.). Also, 30 to 50% of the patients who permits the continuous administration are the nonresponders and often aggravated with this therapy. These facts mean that patients with RRMS include a subgroup that should avoid receiving IFN-β, whereas it is difficult to predict patients not suitable for IFN-β (IFN-β-nonresponsive patient) before administration of IFN-β.

The process of confirming suitability of therapy with IFN-β is afflicting for such patients not suitable for IFN-β. Specifically, cases that discontinue the administration due to a serious adverse reaction or the aggravation of concomitant immune disorder are found not suitable only after an attempt of administration of IFN-β and the subsequent manifestation of these events. The continuous administration, if possible, requires a length of treatment on the order of at least half a year to 1 year for determining its therapeutic effect. Since the mode of administration of IFN-β preparations is self-injection (intramuscular injection or subcutaneous injection), this administration is painful and, in addition, the patients must endure influenza-like symptoms or an adverse reaction, such as headache, required for some additional treatment, though the administration might not be discontinued.

Thus, there has been a strong demand for the development of a method for predicting the therapeutic effect of IFN-β, the manifestation of a serious adverse reaction, and the aggravation of concomitant immune disorder before the start of treatment in order to avoid painful, unnecessary medication for patients not suitable for IFN-β and to appropriately select a suitable patient. In addition, the patients not suitable for IFN-β are often difficult to treat even with other drugs. Thus, it has also been required to establish a novel treatment method for these patients.

A method which involves measuring the expression level of a particular gene group in leukocytes derived from the peripheral blood of a patient by use of a DNA chip or the like has previously been reported as a method for predicting the therapeutic effect of IFN-β on RRMS (Patent Literature 1).

Plasmablasts (PB) are a subset of B cells serving as one type of lymphocyte and have the function of specializing in antibody production. Neuromyelitis optica (NMO), an autoimmune disease of the central nervous system, is clinically important to differentiate from MS, though differing in pathological condition from MS. PB has been identified as a source of production of an autoantibody anti-aquaporin 4 antibody (anti-AQP4 antibody) deeply involved in the pathogenesis of NMO, and has been reported to be increased in the peripheral blood of NMO patients (Non Patent Literature 2). The survival of NMO patient-derived PB and its ability to produce the anti-AQP4 antibody are also known to be promoted in a manner dependent on interleukin 6 (IL-6) (Non Patent Literature 2). It has been reported so far: typical RRMS patients have a peripheral blood PB frequency equivalent to that of healthy persons (Non Patent Literature 2); and increase in PB is found in the peripheral blood of SPMS patients (Non Patent Literature 3). Nonetheless, the relationship between PB in RRMS and prognosis for treatment with IFN-β has not yet been known. Previous pathological research on foci in the MS brain has suggested the involvement of an autoantibody on the formation of such foci (Non Patent Literature 4). Recently, the presence of a disease-specific autoantibody in the serum of MS (including RRMS) patients has been reported (Non Patent Literature 5). Nonetheless, the role of PB in the confirmation of suitability for the treatment method for RRMS has not yet been revealed.

PRIOR ART LITERATURES

Patent Literature

Patent Literature 1: Japanese Patent Application Kokai Publication No. (JP-A) 2004-28926 (unexamined, published Japanese patent application)

Non Patent Literature

Non Patent Literature 1: J Neurol Sci 2012; 323 (1-2): 117-122
Non Patent Literature 2: Proc Natl Acad Sci USA 2011; 108 (9): 3701-3706
Non Patent Literature 3: Plos One 2013; 8 (3): e57820
Non Patent Literature 4: Ann Neurol 2000; 47 (6): 707-717
Non Patent Literature 5: N Engl J Med 2012; 367 (2): 115-123
Non Patent Literature 6: Mult Scler 2008; 14: 1157-1174
Non Patent Literature 7: Brain 1997; 120: 2059-2069
Non Patent Literature 8: Am J Neuroradiol 2000; 21: 702-706

SUMMARY OF THE INVENTION

Problems to be Solved by the Invention

The present invention has been made in light of such situations. An object of the present invention is to provide a method for predicting the therapeutic effect of IFN-β on a RRMS patient. Another object of the present invention is to provide a method for predicting the therapeutic effect of an IL-6 inhibitor on RRMS.

A further object of the present invention is to provide a novel method for treating RRMS in a RRMS patient not suitable for IFN-β.

Means for Solving the Problems

The present inventors have conducted diligent studies to attain the objects. As mentioned above, the presence of a disease-related autoantibody in the serum of MS (including RRMS) patients has been reported (Non Patent Literature 5). Thus, the present inventors have conducted studies based on the hypothesis that autoantibody-producing PB have some involvement in the pathological condition of RRMS. As a result, the present inventors have found that the amount of PB in the peripheral blood of RRMS patients correlates with the therapeutic effect of IFN-β on RRMS. Specifically, the present inventors have found that RRMS patients having a high amount of PB in peripheral blood preferentially include IFN-β-resistant patients, patients with a serious adverse reaction associated with IFN-β, and patients not suitable for IFN-β because of having an additional concomitant immune disorder centering on an autoimmune disorder, whereas peripheral blood collected from patients responsive to treatment with IFN-β is free from such a high amount of PB. The present inventors have further found that PB derived from patients having a high amount of PB in peripheral blood have high responsiveness to IL-6 and survive in an IL-6 dependent-manner.

The present invention is based on these findings and specifically includes the following aspects:

[1]
Use of a plasmablast in the determination of the therapeutic effect of interferon beta on relapsing-remitting multiple sclerosis and/or in the determination of the therapeutic effect of an IL-6 inhibitor on relapsing-remitting multiple sclerosis.

[2]
A method for predicting the therapeutic effect of interferon beta on a relapsing-remitting multiple sclerosis patient, the method comprising the steps of:
(i) measuring an amount of a plasmablast contained in a biological sample isolated from the relapsing-remitting multiple sclerosis patient; and
(ii) showing that the therapeutic effect of the interferon beta is low when the amount of a plasmablast is high as compared with a healthy individual.

[3]
A method for predicting the therapeutic effect of an IL-6 inhibitor on a relapsing-remitting multiple sclerosis patient, the method comprising the steps of:
(i) measuring an amount of a plasmablast contained in a biological sample isolated from the relapsing-remitting multiple sclerosis patient; and
(ii) showing that the therapeutic effect of the IL-6 inhibitor is high when the amount of a plasmablast is high as compared with a healthy individual.

[4]
The use according to [1] or the method according to [3], wherein the IL-6 inhibitor is an anti-IL-6 receptor antibody.

[5]
The use or the method according to [4], wherein the anti-IL-6 receptor antibody is a chimeric antibody, a humanized antibody, or a human antibody.

[6]
The method according to [2] or [3] or the use or the method according to [4] or [5], wherein it is determined that the amount of a plasmablast is high when the ratio of the plasmablast to a CD19$^+$ B cell is 3.50% or more.

[7]
A therapeutic agent for relapsing-remitting multiple sclerosis highly expressing a plasmablast, comprising an IL-6 inhibitor as an active ingredient.

[8]
The therapeutic agent according to [7], wherein the IL-6 inhibitor is an anti-IL-6 receptor antibody.

[9]
The therapeutic agent according to [8], wherein the anti-IL-6 receptor antibody is a chimeric antibody, a humanized antibody, or a human antibody.

Effects of Invention

The present invention provides a method for predicting the therapeutic effect of IFN-β on a RRMS patient by using PB as an index. The method of the present invention allows the avoidance of administration of IFN-β to a patient who cannot be expected to receive the therapeutic effect of IFN-β or who is forced into manifestation of a serious adverse reaction or aggravation of concomitant immune disorder, and can select a treatment method appropriate for the patient. According to the present invention, the therapeutic effect of an IL-6 inhibitor on RRMS can also be predicted by using PB as an index. The method of the present invention can select RRMS patients responsive to treatment with an IL-6 inhibitor, and can also provide a treatment method effective for patients not suitable for treatment with IFN-β.

BRIEF DESCRIPTION OF THE DRAWINGS

FIG. 1 is a diagram showing the measurement of PB by flow cytometry using peripheral blood mononuclear cells (PBMC). A CD3⁻CD14⁻ fraction in FIG. 1A was analyzed for the expression of CD19 and CD27 (FIG. 1B). A CD19⁺CD27⁺ fraction in FIG. 1B was analyzed for the expression of CD180 and CD38 (FIG. 1C) to identify PB (CD19⁺CD27⁺CD180⁻CD38$^{high}$). In this diagram, the amount of PB in peripheral blood was indicated by the ratio (%) of the number of PB to the number of CD19⁺ B cells in peripheral blood.

FIG. 2 is a diagram showing the distribution of the amount of PB in peripheral blood in RRMS patient groups or a healthy individual group.

FIG. 4 is a diagram showing the ratio of IL-6 receptor (IL-6R)-expressing cells in PB in RRMS peripheral blood. FIG. 4A shows a typical histogram of IL-6R expression in PB.

FIG. 5 is a diagram showing the relationship between the survival of PB separated from the peripheral blood of RRMS subgroups (PB-low MS and PB-high MS) and IL-6. FIG. 5B shows the survival rate of PB derived from all RRMS cases, PB-low MS, or PB-high MS, wherein PB was cultured for 2 days in the absence of IL-6 or in the presence of IL-6.

FIG. 6 is a diagram showing change in the amount of PB caused by an anti-IL-6 receptor antibody.

MODE FOR CARRYING OUT THE INVENTION

Figure 2B:
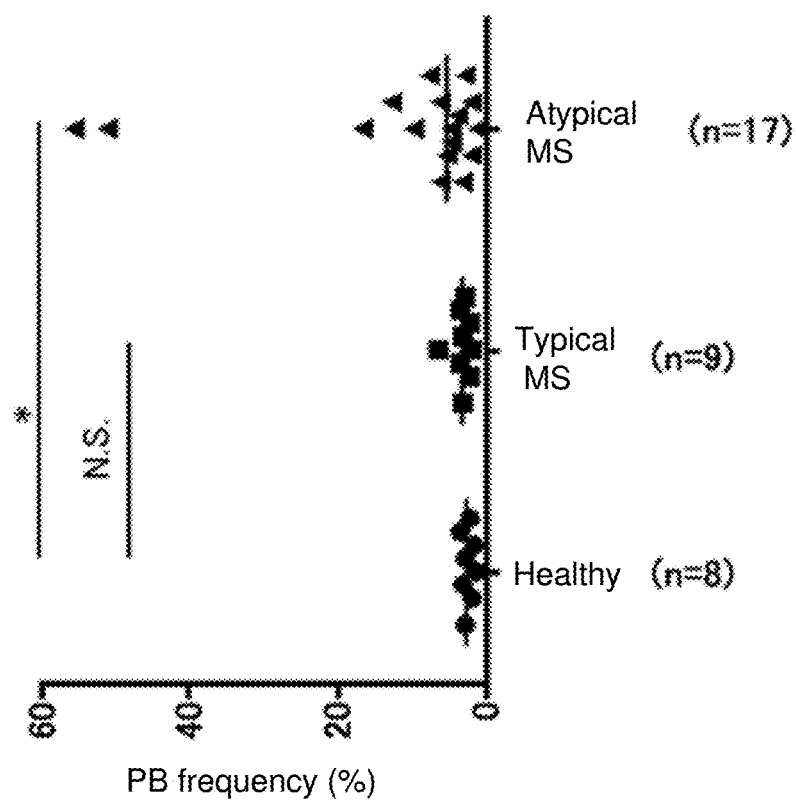
FIG. 2B shows the distribution for untreated subjects.

Hereinafter, the present invention will be described in detail.

The present invention relates to a marker for the determination of the therapeutic effect of interferon beta on relapsing-remitting multiple sclerosis. The present invention also relates to a marker for the determination of suitability for the treatment of relapsing-remitting multiple sclerosis with an IL-6 inhibitor. In the present invention, the therapeutic effect on relapsing-remitting multiple sclerosis or the suitability for the treatment is predicted or determined by using, as an index, the amount of PB (plasmablast) in a biological sample derived from a relapsing-remitting multiple sclerosis patient.

Specifically, the present invention relates to
use of a plasmablast in the determination of the therapeutic effect of interferon beta on relapsing-remitting multiple sclerosis, the use comprising:
(i) measuring an amount of a plasmablast contained in a biological sample isolated from a relapsing-remitting multiple sclerosis patient; and
(ii) showing that the therapeutic effect of the interferon beta is low when the amount of a plasmablast is high as compared with a healthy individual.

The present invention also relates to
use of a plasmablast in the determination of the therapeutic effect of an IL-6 inhibitor on relapsing-remitting multiple sclerosis, the use comprising:
(i) measuring an amount of a plasmablast contained in a biological sample isolated from a relapsing-remitting multiple sclerosis patient; and
(ii) showing that the therapeutic effect of the IL-6 inhibitor is high when the amount of a plasmablast is high as compared with a healthy individual.

Alternatively, the present invention relates to
a method for predicting the therapeutic effect of interferon beta on a relapsing-remitting multiple sclerosis patient, the method comprising the steps of:
(i) measuring an amount of a plasmablast contained in a biological sample isolated from the relapsing-remitting multiple sclerosis patient; and
(ii) showing that the therapeutic effect of the interferon beta is low when the amount of a plasmablast is high as compared with a healthy individual.

The method of the present invention can further comprise, after the step (ii), the step of (iii) administering the interferon beta to a relapsing-remitting multiple sclerosis patient who has not been found low responsive to treatment with the interferon beta.

Specifically, the present invention relates to a method for treating relapsing-remitting multiple sclerosis, comprising the steps (i) to (iii).

Alternatively, the present invention relates to
use of a plasmablast detection reagent in the production of an agent for predicting the therapeutic effect of interferon beta on relapsing-remitting multiple sclerosis.

Alternatively, the present invention relates to
use of a plasmablast detection reagent in the prediction or determination of the therapeutic effect of interferon beta on relapsing-remitting multiple sclerosis.

Alternatively, the present invention relates to
use of a plasmablast detection reagent in the prediction or determination of the therapeutic effect of interferon beta on relapsing-remitting multiple sclerosis, the use comprising:
(i) measuring an amount of a plasmablast contained in a biological sample isolated from a relapsing-remitting multiple sclerosis patient;
(ii) showing that the therapeutic effect of the interferon beta is low when the amount of a plasmablast is high as compared with a healthy individual; and
(iii) administering the interferon beta to a relapsing-remitting multiple sclerosis patient who has not been found low responsive to treatment with the interferon beta.

The present invention also relates to use of interferon beta in the treatment of relapsing-remitting multiple sclerosis, the use comprising:

(i) measuring an amount of a plasmablast contained in a biological sample isolated from a relapsing-remitting multiple sclerosis patient;

(ii) showing that the therapeutic effect of the interferon beta is low when the amount of a plasmablast is high as compared with a healthy individual; and (iii) administering the interferon beta to a relapsing-remitting multiple sclerosis patient who has not been found low responsive to treatment with the interferon beta.

Alternatively, the present invention relates to, use of a plasmablast detection reagent in the production of an agent for predicting the therapeutic effect of interferon beta on relapsing-remitting multiple sclerosis, the use comprising:

(i) measuring an amount of a plasmablast contained in a biological sample isolated from a relapsing-remitting multiple sclerosis patient;

(ii) showing that the therapeutic effect of the interferon beta is low when the amount of a plasmablast is high as compared with a healthy individual; and (iii) administering the interferon beta to a relapsing-remitting multiple sclerosis patient who has not been found low responsive to treatment with the interferon beta.

The present invention also relates to use of interferon beta in the production of a therapeutic agent for relapsing-remitting multiple sclerosis, the use comprising:

(i) measuring an amount of a plasmablast contained in a biological sample isolated from a relapsing-remitting multiple sclerosis patient;

(ii) showing that the therapeutic effect of the interferon beta is low when the amount of a plasmablast is high as compared with a healthy individual; and (iii) administering the interferon beta to a relapsing-remitting multiple sclerosis patient who has not been found low responsive to treatment with the interferon beta.

Alternatively, the present invention relates to a method for detecting a marker for the prediction of the therapeutic effect of interferon beta on relapsing-remitting multiple sclerosis, the method comprising the step of measuring an amount of a plasmablast contained in a biological sample isolated from a relapsing-remitting multiple sclerosis patient.

Alternatively, the present invention relates to interferon beta or a therapeutic agent for relapsing-remitting multiple sclerosis for use in administration to a relapsing-remitting multiple sclerosis patient who has not been found low responsive to treatment with the interferon beta by a method comprising the following steps or for use in the treatment of relapsing-remitting multiple sclerosis which has not been found low responsive to treatment with the interferon beta by a method comprising the following steps:

(i) measuring an amount of a plasmablast contained in a biological sample isolated from a relapsing-remitting multiple sclerosis patient; and (ii) showing that the therapeutic effect of the interferon beta is low when the amount of a plasmablast is high as compared with a healthy individual.

The method of the present invention can further comprise, after the step (ii), the step of (iii) administering the interferon beta or the therapeutic agent for relapsing-remitting multiple sclerosis to a relapsing-remitting multiple sclerosis patient who has not been found low responsive to treatment with the interferon beta.

Alternatively, the present invention relates to a therapeutic agent for relapsing-remitting multiple sclerosis which is directed to:

(i) measuring an amount of a plasmablast contained in a biological sample isolated from a relapsing-remitting multiple sclerosis patient;

(ii) showing that the therapeutic effect of the interferon beta is low when the amount of a plasmablast is high as compared with a healthy individual; and (iii) administering the therapeutic agent for relapsing-remitting multiple sclerosis to a relapsing-remitting multiple sclerosis patient who has not been found low responsive to treatment with the interferon beta, the therapeutic agent for relapsing-remitting multiple sclerosis comprising the interferon beta as an active ingredient.

Alternatively, the present invention relates to an agent for predicting the therapeutic effect of interferon beta on relapsing-remitting multiple sclerosis which is directed to:

(i) measuring an amount of a plasmablast contained in a biological sample isolated from a relapsing-remitting multiple sclerosis patient;

(ii) showing that the therapeutic effect of the interferon beta is low when the amount of a plasmablast is high as compared with a healthy individual; and (iii) administering the interferon beta to a relapsing-remitting multiple sclerosis patient who has not been found low responsive to treatment with the interferon beta, the predicting agent comprising a plasmablast detection reagent.

The present invention also relates to a method for predicting the therapeutic effect of an IL-6 inhibitor on a relapsing-remitting multiple sclerosis patient, the method comprising the steps of:

(i) measuring an amount of a plasmablast contained in a biological sample isolated from the relapsing-remitting multiple sclerosis patient; and (ii) showing that the therapeutic effect of the IL-6 inhibitor is high when the amount of a plasmablast is high as compared with a healthy individual.

The method of the present invention can further comprise, after the step (ii), the step of (iii) administering the IL-6 inhibitor to a relapsing-remitting multiple sclerosis patient who has been found highly responsive to treatment with the IL-6 inhibitor.

Specifically, the present invention relates to a method for treating relapsing-remitting multiple sclerosis, comprising the steps (i) to (iii).

Alternatively, the present invention relates to use of a plasmablast detection reagent in the production of an agent for predicting the therapeutic effect of an IL-6 inhibitor on relapsing-remitting multiple sclerosis.

Alternatively, the present invention relates to use of a plasmablast detection reagent in the prediction or determination of the therapeutic effect of an IL-6 inhibitor on relapsing-remitting multiple sclerosis.

Alternatively, the present invention relates to use of a plasmablast detection reagent in the prediction or determination of the therapeutic effect of an IL-6 inhibitor on relapsing-remitting multiple sclerosis, the use comprising:

(i) measuring an amount of a plasmablast contained in a biological sample isolated from a relapsing-remitting multiple sclerosis patient;

(ii) showing that the therapeutic effect of the IL-6 inhibitor is high when the amount of a plasmablast is high as compared with a healthy individual; and (iii) administering the IL-6 inhibitor to a relapsing-remitting multiple sclerosis patient who has been found highly responsive to treatment with the IL-6 inhibitor.

The present invention also relates to use of an IL-6 inhibitor in the treatment of relapsing-remitting multiple sclerosis, the use comprising:
(i) measuring an amount of a plasmablast contained in a biological sample isolated from a relapsing-remitting multiple sclerosis patient;
(ii) showing that the therapeutic effect of the IL-6 inhibitor is high when the amount of a plasmablast is high as compared with a healthy individual; and
(iii) administering the IL-6 inhibitor to a relapsing-remitting multiple sclerosis patient who has been found highly responsive to treatment with the IL-6 inhibitor.

Alternatively, the present invention relates to use of a plasmablast detection reagent in the production of an agent for predicting the therapeutic effect of an IL-6 inhibitor on relapsing-remitting multiple sclerosis, the use comprising:
(i) measuring an amount of a plasmablast contained in a biological sample isolated from a relapsing-remitting multiple sclerosis patient;
(ii) showing that the therapeutic effect of the IL-6 inhibitor is high when the amount of a plasmablast is high as compared with a healthy individual; and
(iii) administering the IL-6 inhibitor to a relapsing-remitting multiple sclerosis patient who has been found highly responsive to treatment with the IL-6 inhibitor.

The present invention also relates to use of an IL-6 inhibitor in the production of a therapeutic agent for relapsing-remitting multiple sclerosis, the use comprising:
(i) measuring an amount of a plasmablast contained in a biological sample isolated from a relapsing-remitting multiple sclerosis patient;
(ii) showing that the therapeutic effect of the IL-6 inhibitor is high when the amount of a plasmablast is high as compared with a healthy individual; and
(iii) administering the IL-6 inhibitor to a relapsing-remitting multiple sclerosis patient who has been found highly responsive to treatment with the IL-6 inhibitor.

Alternatively, the present invention relates to a method for detecting a marker for the prediction of the therapeutic effect of an IL-6 inhibitor on relapsing-remitting multiple sclerosis, the method comprising the step of measuring an amount of a plasmablast contained in a biological sample isolated from a relapsing-remitting multiple sclerosis patient.

Alternatively, the present invention relates to an IL-6 inhibitor or a therapeutic agent for relapsing-remitting multiple sclerosis for use in administration to a relapsing-remitting multiple sclerosis patient who has been found highly responsive to treatment with the IL-6 inhibitor by a method comprising the following steps or for use in the treatment of relapsing-remitting multiple sclerosis which has been found highly responsive to treatment with the IL-6 inhibitor by a method comprising the following steps:
(i) measuring an amount of a plasmablast contained in a biological sample isolated from a relapsing-remitting multiple sclerosis patient; and
(ii) showing that the therapeutic effect of the IL-6 inhibitor is high when the amount of a plasmablast is high as compared with a healthy individual.

The method of the present invention can further comprise, after the step (ii), the step of (iii) administering the IL-6 inhibitor or the therapeutic agent for relapsing-remitting multiple sclerosis to a relapsing-remitting multiple sclerosis patient who has been found highly responsive to treatment with the IL-6 inhibitor.

Alternatively, the present invention relates to a therapeutic agent for relapsing-remitting multiple sclerosis which is directed to:
(i) measuring an amount of a plasmablast contained in a biological sample isolated from a relapsing-remitting multiple sclerosis patient;
(ii) showing that the therapeutic effect of the IL-6 inhibitor is high when the amount of a plasmablast is high as compared with a healthy individual; and
(iii) administering the therapeutic agent for relapsing-remitting multiple sclerosis to a relapsing-remitting multiple sclerosis patient who has been found highly responsive to treatment with the IL-6 inhibitor, the therapeutic agent for relapsing-remitting multiple sclerosis comprising the IL-6 inhibitor as an active ingredient.

Alternatively, the present invention relates to an agent for predicting the therapeutic effect of an IL-6 inhibitor on relapsing-remitting multiple sclerosis which is directed to:
(i) measuring an amount of a plasmablast contained in a biological sample isolated from a relapsing-remitting multiple sclerosis patient;
(ii) showing that the therapeutic effect of the IL-6 inhibitor is high when the amount of a plasmablast is high as compared with a healthy individual; and
(iii) administering the IL-6 inhibitor to a relapsing-remitting multiple sclerosis patient who has been found highly responsive to treatment with the IL-6 inhibitor, the predicting agent comprising a plasmablast detection reagent.

In the present invention, the method for predicting the therapeutic effect can also be used interchangeably with a method for predicting prognosis, a method for determining suitability for treatment, a method for diagnosing the therapeutic effect, etc.

In the present invention, the phrases "found low responsive to treatment" and "found highly responsive to treatment" can also be used interchangeably with the phrases "confirmed to be low responsive to treatment" and "confirmed to be highly responsive to treatment", respectively.

In the present invention, the "relapsing-remitting multiple sclerosis patient who has not been found low responsive to treatment with the interferon beta" can be used interchangeably with a "patient suitable for treatment with the interferon beta", an "interferon beta-responsive patient", etc. The present invention relates to a method for identifying a patient suitable for the treatment of relapsing-remitting multiple sclerosis with interferon beta, the method comprising the steps of:
(i) measuring an amount of a plasmablast contained in a biological sample isolated from a relapsing-remitting multiple sclerosis patient; and
(ii) showing that the therapeutic effect of the interferon beta is low when the amount of a plasmablast is high as compared with a healthy individual.

In the present invention, the "relapsing-remitting multiple sclerosis patient who has been found highly responsive to treatment with the IL-6 inhibitor" can be used interchangeably with a "patient suitable for treatment with the IL-6 inhibitor", an "IL-6 inhibitor-responsive patient", a "patient not suitable for treatment with interferon beta", an "interferon beta-nonresponsive patient", etc. The present invention relates to a method for identifying a patient suitable for the treatment of relapsing-remitting multiple sclerosis with an IL-6 inhibitor, the method comprising the steps of:
(i) measuring an amount of a plasmablast contained in a biological sample isolated from a relapsing-remitting multiple sclerosis patient; and
(ii) showing that the therapeutic effect of the IL-6 inhibitor is high when the amount of a plasmablast is high as compared with a healthy individual.

In the present invention, the amount of a plasmablast (PB) contained in a biological sample isolated from a relapsing-remitting multiple sclerosis patient is measured. The "biological sample" according to the present invention is not particularly limited as long as the biological sample can be collected from the patient and permits measurement of the amount of PB. Examples of such a sample can include, but are not limited to, blood-derived samples. The blood-derived samples are not limited as long as the blood-derived samples contain lymphocytes. Examples thereof preferably include peripheral blood and whole blood and particularly preferably include peripheral blood. Methods for obtaining the blood-derived samples from test subjects are well known to those skilled in the art.

In the present invention, the relapsing-remitting multiple sclerosis refers to multiple sclerosis with repetitive relapses and remissions. In the present invention, the relapsing-remitting multiple sclerosis patient can also be referred to as a "test subject suspected of having relapsing-remitting multiple sclerosis" or a "patient in need of the treatment of relapsing-remitting multiple sclerosis". The "relapsing-remitting multiple sclerosis patient" of the present invention can be, but is not limited to, a relapsing-remitting multiple sclerosis patient without neuromyelitis optica.

Plasmablasts (PB) are a subset of B cells serving as one type of lymphocyte and have the function of specializing in antibody production. Examples of the "plasmablast (PB)" according to the present invention include, but are not limited to, B cells exhibiting $CD19^+CD27^+CD180^-CD38^{high}$ expression. In the present invention, the "amount of a plasmablast (PB)" refers to the number of cells of or the ratio of the plasmablast. Specifically, for example, the ratio of the number of the plasmablast (PB) to the number of $CD19^+$ B cells in peripheral blood can be indicated by (the number of the plasmablast (PB)/the number of $CD19^+$ B cells×100(%)). In the present invention, the amount of a plasmablast (PB) can also be referred to as the ratio of the number of the plasmablast (PB) to the number of $CD19^+$ B cells or simply as the ratio of the plasmablast (PB), etc.

In the present invention, the phrase "the amount of a plasmablast (PB) is high" or "a high amount of a plasmablast (PB)" means that the amount of PB contained in a biological sample isolated from a relapsing-remitting multiple sclerosis patient is equal to or higher than the average amount of PB+1SD (SD: standard deviation), more preferably 2SD (SD: standard deviation), in healthy individuals. On the other hand, the phrase "the amount of a plasmablast (PB) is low" or "a low amount of a plasmablast (PB)" means that the amount of PB is lower than this reference value. In the present invention, in the case where the amount of a plasmablast contained in a biological sample isolated from a relapsing-remitting multiple sclerosis patient is indicated by the aforementioned ratio of the number of the plasmablast (PB) to the number of $CD19^+$ B cells in peripheral blood (the number of the plasmablast (PB)/the number of $CD19^+$ B cells×100(%)), it is shown that the amount of a plasmablast is high when this ratio is, for example, 3.00% or more, preferably 3.50% or more, particularly preferably 3.94% or more, more preferably 4.50% or more.

In the present invention, it is shown that the therapeutic effect of interferon beta on relapsing-remitting multiple sclerosis is low when the amount of a plasmablast is high. Also, it is shown that the therapeutic effect of an IL-6 inhibitor on relapsing-remitting multiple sclerosis is high when the amount of a plasmablast is high.

In the present invention, the phrase "low responsive to the treatment of relapsing-remitting multiple sclerosis with interferon beta" means that at least any one of the following conditions is satisfied:
the number of relapses within 2 years after the start of the treatment with interferon beta is 2 or more;
a serious adverse reaction is manifested; and
concomitant immune disorder centering on an autoimmune disorder aggravated by the interferon beta is present.

The method for measuring the amount of PB according to the present invention is not particularly limited and can be carried out, for example, by measuring the amount of B cells in peripheral blood isolated from the patient by flow cytometry analysis using fluorescently labeled antibodies. Specifically, peripheral blood mononuclear cells (PBMC) can be co-stained with a fluorescent anti-CD3 antibody (Anti-CD3-PerCP-Cy5.5: BioLegend, Inc., 300430), a fluorescent anti-CD14 antibody (Anti-CD14-APC: BioLegend, Inc., 301808), a fluorescent anti-CD19 antibody (Anti-CD19-APC-Cy7, BD Biosciences, 348794), a fluorescent anti-CD27 antibody (Anti-CD27-PE-Cy7, BD Biosciences, 560609), a fluorescent anti-CD180 antibody (Anti-CD180-PE, BD Biosciences, 551953), and a fluorescent anti-CD38 antibody (anti-CD38-FITC, Beckman Coulter, Inc., A0778) to select cells exhibiting $CD19^+CD27^+CD180^-CD38^{high}$ expression.

More specifically, for example, $CD3^+$ T cells or $CD14^+$ monocytes are excluded from PBMC, and $CD19^+CD27^+$ cells are selected. $CD180^-CD38^{high}$ cells can be further selected to obtain $CD19^+CD27^+CD180^-CD38^{high}$ cells. For example, cells having a CD19 expression level of $10^3$ or higher are defined as $CD19^+$ cells; B cells having a CD27 expression level of $2\times10^3$ or higher are defined as $CD27^+$ cells; B cells having a CD180 expression level of $2\times10^3$ or lower are defined as $CD180^-$ cells; and B cells having a CD38 expression level of $3\times10^3$ or higher are defined as $CD38^{high}$ cells. According to these criteria, $CD19^+CD27^+CD180^-CD38^{high}$ cells can be obtained. Also, the cells having a CD19 expression level of $10^3$ or higher can be defined as $CD19^+$ B cells. The amount of PB can be determined, as mentioned above, according to the number of $CD19^+CD27^+CD180^-CD38^{high}$ B cells/the number of $CD19^+$ B cells×100(%).

In the present invention, PB can also be detected using a plasmablast detection reagent. The plasmablast detection reagent is not particularly limited as long as the plasmablast detection reagent is capable of detecting the plasmablast. Examples thereof can include antibodies capable of recognizing the plasmablast. The antibodies capable of recognizing the plasmablast are not particularly limited as long as the antibodies can recognize a protein or a receptor expressed on the surface of the plasmablast. Examples thereof include an anti-CD19 antibody, a CD27 antibody, and an anti-CD38 antibody. In the present invention, two or more of these antibodies or all of the three antibodies are preferably used in combination.

The antibody of the present invention can be a polyclonal antibody or a monoclonal antibody. Alternatively, the antibody of the present invention may be a multispecific antibody recognizing two or more different antigenic determinants such as proteins or receptors expressed on the surface of the plasmablast.

The present invention provides even a kit for detecting a marker for the prediction of a therapeutic effect on relapsing-remitting multiple sclerosis, the kit comprising: (i) a reagent for detecting a plasmablast in a biological sample; and (ii) a positive control sample for the plasmablast.

The kit of the present invention is a kit for detecting a marker for the prediction of a therapeutic effect on relapsing-remitting multiple sclerosis which is directed to:
(i) measuring an amount of a plasmablast contained in a biological sample isolated from a relapsing-remitting multiple sclerosis patient;
(ii) showing that the therapeutic effect of interferon beta is low when the amount of a plasmablast is high as compared with a healthy individual; and
(iii) administering the interferon beta to a relapsing-remitting multiple sclerosis patient who has not been found low responsive to treatment with the interferon beta.

The kit of the present invention is also a kit for detecting a marker for the prediction of a therapeutic effect on relapsing-remitting multiple sclerosis which is directed to:
(i) measuring an amount of a plasmablast contained in a biological sample isolated from a relapsing-remitting multiple sclerosis patient;
(ii) showing that the therapeutic effect of an IL-6 inhibitor is high when the amount of a plasmablast is high as compared with a healthy individual; and
(iii) administering the IL-6 inhibitor to a relapsing-remitting multiple sclerosis patient who has been found highly responsive to treatment with the IL-6 inhibitor.

In the present invention, the therapeutic effect of interferon beta is predicted by using PB as an index. The interferon beta of the present invention can be in the form of a protein, the form of a DNA encoding the protein, or the form of a vector having an insert of the DNA. The protein or the DNA can be synthesized by a genetic engineering approach or a chemical approach. Those skilled in the art can obtain a vector having an insert of the DNA encoding interferon beta by use of a vector for gene therapy known in the art.

Those skilled in the art can obtain such a protein, a DNA, or a vector on the basis of the amino acid sequence or the nucleotide sequence of interferon beta known in the art. Also, those skilled in the art can obtain a protein functionally equivalent to interferon beta, a DNA encoding the protein, or a vector having an insert of the DNA by site-directed mutagenesis, PCR, or a hybridization technique known in the art. Alternatively, the interferon beta can be in the form of a preparation mixed with a pharmaceutically acceptable salt known in the art.

The interferon beta can be a natural protein or can be prepared as a recombinant protein by a gene recombination technique known in the art. The recombinant protein can be prepared by a method generally known to those skilled in the art. The recombinant protein can be prepared, for example, by incorporating a nucleic acid encoding interferon beta into appropriate expression vectors, which are then transferred to appropriate host cells, recovering the resulting transformants, obtaining extracts, and then purifying the protein by, for example, ion-exchange, reverse-phase, or gel filtration chromatography or affinity chromatography using an anti-interferon beta antibody-immobilized column or by the combined use of a plurality of columns therefor.

In the case of allowing the interferon beta to be expressed within host cells (e.g., animal cells or *E. coli*) as a fusion polypeptide with glutathione S-transferase protein or as a recombinant polypeptide with a plurality of histidine residues added thereto, the expressed recombinant polypeptide can be purified using a glutathione column or a nickel column.

In the case of using, for example, *E. coli*, as a host, the vector is not particularly limited as long as the vector has "ori" for amplification in *E. coli* in order to amplify and prepare the vector in a large amount in *E. coli* (e.g., JM109, DH5α, HB101, or XL1-Blue) and further has a marker gene (e.g., a drug resistance gene that is identifiable by a certain drug (ampicillin, tetracycline, kanamycin, or chloramphenicol)) for transformed *E. coli*. Examples of the vector include M13-series vectors, pUC-series vector, pBR322, pBluescript, and pCR-Script. For the purpose of cDNA subcloning and excision, examples thereof include the vectors mentioned above as well as pGEM-T, pDIRECT, and pT7. In the case of using the vector for the purpose of interferon beta production, an expression vector is particularly useful. For the purpose of, for example, expression in *E. coli*, it is essential for the expression vector to have the aforementioned features for the amplification of the vector in *E. coli* as well as to have a promoter that permits efficient expression in *E. coli* such as JM109, DH5α, HB101, or XL1-Blue used as a host, for example, lacZ promoter (Ward et al., Nature (1989) 341, 544-546; and FASEB J. (1992) 6, 2422-2427), araB promoter (Better et al., Science (1988) 240, 1041-1043), or T7 promoter. Examples of such a vector include the vectors mentioned above as well as pGEX-5X-1 (manufactured by Pharmacia Corp.), "QIAexpress system" (manufactured by Qiagen N.V.), pEGFP, and pET.

The vector may also contain a signal sequence for polypeptide secretion. For production in the periplasm of *E. coli*, a pelB signal sequence (Lei, S. P. et al J. Bacteriol. (1987) 169, 4379) can be used as the signal sequence for polypeptide secretion. The vector can be transferred to the host cells by use of, for example, a calcium chloride method or electroporation.

Examples of expression vectors other than the *E. coli*-derived expression vectors include mammal-derived expression vectors (e.g., pcDNA3 (manufactured by Invitrogen Corp.), pEGF-BOS (Nucleic Acids. Res. 1990, 18 (17), p. 5322), pEF, and pCDM8), insect cell-derived expression vectors (e.g., "Bac-to-BAC baculovirus expression system" (manufactured by Gibco BRL/Life Technologies, Inc.) and pBacPAK8), plant-derived expression vectors (e.g., pMH1 and pMH2), animal virus-derived expression vectors (e.g., pHSV, pMV, and pAdexLcw), retrovirus-derived expression vectors (e.g., pZIPneo), yeast-derived expression vectors (e.g., "*Pichia* Expression Kit" (manufactured by Invitrogen Corp.), pNV11, and SP-Q01), and *Bacillus subtilis*-derived expression vectors (e.g., pPL608 and pKTH50).

For the purpose of expression in animal cells such as CHO cells, COS cells, or NIH3T3 cells, it is essential for the expression vector to have a promoter necessary for intracellular expression, for example, SV40 promoter (Mulligan et al., Nature (1979) 277, 108), MMLV-LTR promoter, EF1α promoter (Mizushima et al., Nucleic Acids Res. (1990) 18, 5322), or CMV promoter and more preferred to have a marker gene (e.g., a drug resistance gene that is identifiable by a drug (neomycin, G418, etc.)) for transformed cells. Examples of vectors having such properties include pMAM, pDR2, pBK-RSV, pBK-CMV, pOPRSV, and pOP13.

Examples of systems for producing the polypeptide in vivo include production systems using animals and production systems using plants. A nucleic acid encoding interferon beta is transferred to such an animal or a plant, and the interferon beta is produced in the body of the animal or the plant and recovered.

In the case of using the animal, a mammal or an insect can be used in the production system. A goat, a pig, sheep, a mouse, or cattle can be used as the mammal (Vicki Glaser, SPECTRUM Biotechnology Applications, 1993). In the case of using the mammal, a transgenic animal can be used.

The interferon beta thus obtained can be isolated from the inside of the host cells or the outside of the cells (medium, etc.) and purified as a substantially pure and homogeneous polypeptide. The polypeptide separation and purification can be carried out without limitations using a separation and purification method for use in ordinary polypeptide purification. The polypeptide can be separated and purified by appropriately selecting or combining, for example, chromatography columns, filters, ultrafiltration, salting out, solvent precipitation, solvent extraction, distillation, immunoprecipitation, SDS-polyacrylamide gel electrophoresis, isoelectric focusing, dialysis, and/or recrystallization.

Before or after the purification of the interferon beta, an arbitrary modification may be applied thereto or a partial peptide may be removed therefrom by the action of an appropriate protein-modifying enzyme. For example, trypsin, chymotrypsin, lysyl endopeptidase, protein kinase, or glucosidase is used as the protein-modifying enzyme.

The interferon beta also includes a protein that has undergone the alteration of one or more amino acids and has the potential function of serving as interferon beta after activation of the interferon beta. Within this scope, the interferon beta also includes an interferon beta fragment.

In the case of altering the amino acid residues, each amino acid is desirably varied to another amino acid having the same side chain properties thereas. Examples of the amino acid side chain properties can include hydrophobic amino acids (A, I, L, M, F, P, W, Y, and V), hydrophilic amino acids (R, D, N, C, E, Q, G, H, K, S, and T), amino acids having an aliphatic side chain (G, A, V, L, I, and P), amino acids having a hydroxy group-containing side chain (S, T, and Y), amino acids having a sulfur atom-containing side chain (C and M), amino acids having carboxylic acid- and amide-containing side chain (D, N, E, and Q), amino acids having a base-containing side chain (R, K, and H), and amino acids having an aromatic group-containing side chain (H, F, Y, and W) (the one-letter codes of these amino acids are indicated within the parentheses). The amino acid substitution within each of these groups is referred to as conservative substitution. It has already been known that a polypeptide having an amino acid sequence modified from a certain amino acid sequence by the deletion and/or addition of one or more (e.g., 2, 3, 4, 5, 10, 20, 30, 40, 50, or 100) amino acid residues and/or the substitution thereof with other amino acids maintains its biological activity (Mark, D. F. et al., Proc. Natl. Acad. Sci. USA (1984) 81: 5662-6; Zoller, M. J. and Smith, M., Nucleic Acids Res. (1982) 10: 6487-500; Wang, A. et al., Science (1984) 224: 1431-3; and Dalbadie-McFarland, G. et al., Proc. Natl. Acad. Sci. USA (1982) 79: 6409-13). Such a variant has at least 70%, preferably at least 75%, more preferably at least 80%, further preferably at least 85%, still further preferably at least 90%, most preferably at least 95% amino acid sequence identity to the amino acid sequence of the interferon beta before the amino acid alteration or a fragment of the interferon beta. In the present specification, the sequence identity is determined by aligning the sequences to be compared according to the need so as to attain the maximum sequence identity and appropriately introducing a gap thereto, and defined as the ratio of the number of identical residues to the number of residues in the amino acid sequence of the original heavy chain variable region or light chain variable region.

The amino acid sequence or nucleotide sequence identity can be determined using the algorithm BLAST of Karlin and Altschul (Proc. Natl. Acad. Sci. USA 87: 2264-2268, 1990; and Proc Natl Acad Sci USA 90: 5873, 1993). A program called BLASTN or BLASTX based on the algorithm of BLAST has been developed (Altschul S F, et al., J Mol Biol 215: 403, 1990). In the case of analyzing nucleotide sequences using BLASTN, the parameters are set to, for example, score=100 and wordlength=12. In the case of analyzing amino acid sequences using BLASTX, the parameters are set to, for example, score=50 and wordlength=3. In the case of using BLAST and Gapped BLAST programs, the default parameters of each program are used. Specific approaches for these analysis methods are known in the art.

As methods for preparing a DNA encoding the protein having an altered amino acid sequence, for example, site-directed mutagenesis (Kramer, W. and Fritz, H.-J. (1987) Oligonucleotide-directed construction of mutagenesis via gapped duplex DNA. Methods in Enzymology, 154: 350-367), a hybridization technique (Southern, E. M. (1975) Journal of Molecular Biology, 98, 503), and a PCR technique (Saiki, R. K. et al., (1985) Science, 230, 1350-1354; and Saiki, R. K. et al., (1988) Science, 239, 487-491) are well known to those skilled in the art, Examples of the "treatment with interferon beta (IFN-β)" according to the present invention can preferably include, but are not limited to, interferon beta with interferon beta-1a (Avonex(R) or interferon beta-1b (Betaferon(R), and treatment with other interferon beta preparations.

In the present invention, the therapeutic effect of an IL-6 inhibitor on relapsing-remitting multiple sclerosis is also predicted by using PB as an index. In the present invention, the "IL-6 inhibitor" is not limited as long as the IL-6 inhibitor is capable of blocking IL-6 signal transduction and inhibiting the biological activity of IL-6. Specific examples of the IL-6 inhibitor can include a substance binding to IL-6, a substance binding to an IL-6 receptor, and a substance binding to gp130. Other examples of the IL-6 inhibitor can include, but are not limited to, a substance inhibiting STATS phosphorylation important as the intracellular signal of IL-6, for example, AG490. The IL-6 inhibitor includes, but is not particularly limited to, an anti-IL-6 antibody, an anti-IL-6 receptor antibody, an anti-gp130 antibody, an IL-6 variant, a soluble IL-6 receptor variant, a partial IL-6 peptide, a partial IL-6 receptor peptide, and a low-molecular compound exhibiting activity similar thereto.

Examples of the preferred form of the IL-6 inhibitor can include an IL-6 receptor inhibitor, particularly an anti-IL-6 receptor antibody.

The origin of the antibody used in the present invention is not particularly limited, and the antibody can be derived from preferably a mammal, more preferably a human.

The antibody used in the present invention can be obtained as a polyclonal or monoclonal antibody by use of an approach known in the art. The antibody used in the present invention is particularly preferably a mammal-derived monoclonal antibody. The mammal-derived monoclonal antibody includes an antibody produced by a hybridoma, and an antibody produced by a host transformed with an expression vector containing an antibody gene by a genetic engineering approach. Usually, this antibody blocks the intracellular transduction of the biological activity of IL-6 through its binding to IL-6, an IL-6 receptor, gp130, or the like.

Basically, the monoclonal antibody-producing hybridoma can be prepared by use of a technique known in the art as follows: an IL-6 receptor, IL-6, gp130, or the like is used as a sensitizing antigen in immunization according to an ordinary immunization method, and the resulting immunocytes can be fused with parent cells known in the art by an ordinary cell fusion method and screened for monoclonal antibody-producing cells by an ordinary screening method to prepare monoclonal antibody-producing hybridomas.

Specifically, the monoclonal antibody can be prepared as follows: in the case of preparing, for example, an anti-IL-6 receptor antibody, the antibody is obtained by using the nucleotide sequence of a gene encoding an IL-6 receptor disclosed in European Patent Application Publication No. EP 325474 as a human IL-6 receptor for use as a sensitizing antigen or disclosed in Japanese Patent Laid-Open No. 3-155795 as a mouse IL-6 receptor for use as a sensitizing antigen, and/or the amino acid sequence of the IL-6 receptor protein.

IL-6 receptor proteins are classified into two types: a protein expressed on the cell membrane, and a protein dissociated from the cell membrane (soluble IL-6 receptor) (Yasukawa, K. et al., J. Biochem. (1990) 108, 673-676). The soluble IL-6 receptor is constituted by substantially the extracellular region of the IL-6 receptor bound with the cell membrane and differs from the membrane-bound IL-6 receptor in that the soluble IL-6 receptor is deficient in the transmembrane region or in the transmembrane region and the intracellular region. Any IL-6 receptor may be used as the IL-6 receptor protein of the present invention as long as the IL-6 receptor may be used as a sensitizing antigen in the preparation of the anti-IL-6 receptor antibody used in the present invention.

The gene sequence of the IL-6 receptor is inserted to an expression vector system known in the art, and appropriate host cells are transformed therewith. Then, the IL-6 receptor protein of interest is purified by a method known in the art from the inside of the host cells or from a culture supernatant thereof. This purified IL-6 receptor protein can be used as the sensitizing antigen. Alternatively, cells expressing the IL-6 receptor or a fusion protein of the IL-6 receptor protein with another protein may be used as the sensitizing antigen.

Likewise, in the case of using IL-6 as a sensitizing antigen in antibody obtainment, the antibody is obtained by using the nucleotide sequence of a gene encoding IL-6 disclosed in Eur. J. Biochem (1987) 168, 543-550, J. Immunol. (1988) 140, 1534-1541, or Agr. Biol. Chem. (1990) 54, 2685-2688 as human IL-6, and/or the amino acid sequence of the IL-6 protein. Also, the nucleotide sequence of a gp130 gene and/or the amino acid sequence of the gp130 protein disclosed in European Patent Application Publication No. EP 411946 can be used as a sensitizing antigen for obtaining the anti-gp130 antibody.

The mammal to be immunized with the sensitizing antigen is not particularly limited and is preferably selected in consideration with compatibility with the parent cells for use in cell fusion. In general, a rodent, for example, a mouse, a rat, or a hamster is used.

The animal is immunized with the sensitizing antigen according to a method known in the art. For example, a general method involves intraperitoneally or subcutaneously injecting the sensitizing antigen to the mammal. Specifically, the sensitizing antigen diluted or suspended in an appropriate amount with or in PBS (phosphate-buffered saline), saline, or the like is mixed, if desired, with an appropriate amount of a usual adjuvant, for example, a complete Freund's adjuvant. After emulsification, several shots of the emulsion are each preferably administered to the mammal every 4 to 21 days. Also, an appropriate carrier can be used in the immunization with the sensitizing antigen.

After such immunization and confirmation of a rise in desired antibody level in serum, immunocytes are collected from the mammal and subjected to cell fusion. Preferred examples of the immunocytes that are subjected to cell fusion particularly include spleen cells.

Mammalian myeloma cells for use as partner parent cells to be fused with the immunocytes have already been known in the art, and various cell lines, for example, P3X63Ag8.653 (Kearney, J. F. et al., J. Immunol. (1979) 123, 1548-1550), P3X63Ag8U.1 (Current Topics in Microbiology and Immunology (1978) 81, 1-7), NS-1 (Kohler. G. and Milstein, C. Eur. J. Immunol. (1976) 6, 511-519), MPC-11 (Margulies. D. H. et al., Cell (1976) 8, 405-415), SP2/0 (Shulman, M. et al., Nature (1978) 276, 269-270), FO (de St. Groth, S. F. et al., J. Immunol. Methods (1980) 35, 1-21), S194 (Trowbridge, I. S. J. Exp. Med. (1978) 148, 313-323), and R210 (Galfre, G. et al., Nature (1979) 277, 131-133) are appropriately used.

Basically, the cell fusion between the immunocytes and the myeloma cells can be carried out according to a method known in the art, for example, the method of Milstein et al. (Kohler. G. and Milstein, C., Methods Enzymol. (1981) 73, 3-46).

More specifically, the cell fusion is carried out, for example, in a usual nutrient medium in the presence of a cell fusion promoter. For example, polyethylene glycol (PEG) or hemagglutinating virus of Japan (HVJ) is used as the fusion promoter. An auxiliary such as dimethyl sulfoxide can be further added thereto and used, if desired, for enhancing fusion efficiency.

The ratio between the immunocytes and the myeloma cells used is preferably set to, for example, 1:1 to 10:1 (immunocytes:myeloma cells). For example, an RPMI1640 medium or a MEM medium suitable for the growth of the myeloma cell lines mentioned above or a usual medium for use in this kind of cell culture can be used as the medium in the cell fusion and may be used in combination with a serum supplement such as fetal calf serum (FCS).

For the cell fusion, predetermined amounts of the immunocytes and the myeloma cells are well mixed in the medium. A PEG solution, for example, a solution of PEG having an average molecular weight on the order of 1000 to 6000, preheated to approximately 37° C. is usually added to the mixture at a concentration of 30 to 60% (w/v) and mixed therewith to form the fusion cells (hybridomas) of interest. Subsequently, the operation of sequentially adding an appropriate medium and removing a supernatant by centrifugation can be repeated to remove cell fusion agents or the like unfavorable for the growth of the hybridomas.

The hybridomas thus obtained are cultured in a usual selective medium, for example, a HAT medium (medium containing hypoxanthine, aminopterin, and thymidine) for selection. This culture in the HAT medium is continued for a period (usually, several days to several weeks) sufficient for killing cells (non-fused cells) other than the hybridomas of interest. Subsequently, hybridomas producing the antibody of interest are screened for and cloned by an ordinary limiting dilution method.

In addition to such obtainment of the hybridomas by the immunization of the non-human animal with the antigen, a desired human antibody having binding activity against the desired antigen or cells expressing the antigen may be obtained by sensitizing in vitro human lymphocytes with the desired antigen protein or cells expressing the antigen and fusing the sensitized B lymphocytes with human myeloma cells, for example, U266 (see Japanese Patent Publication No. 1-59878). Alternatively, the antigen or cells expressing the antigen may be administered to a transgenic animal having human antibody gene repertoires, and the desired human antibody can be obtained according to the method mentioned above (see International Publication Nos. WO93/12227, WO92/03918, WO94/02602, WO94/25585, WO96/34096, and WO96/33735).

The monoclonal antibody-producing hybridomas thus prepared can be subcultured in a usual medium and can also be preserved for a long period in liquid nitrogen.

The monoclonal antibody is obtained from the hybridomas by the adoption of, for example, a method which involves culturing the hybridomas according to an ordinary method and obtaining the antibody as a culture supernatant thereof, or a method which involves administering the hybridomas to mammals compatible therewith and, after growth, obtaining the antibody as ascitic fluid thereof. The former method is suitable for obtaining a highly pure antibody, while the latter method is suitable for the large-scale production of the antibody.

For example, hybridomas producing the anti-IL-6 receptor antibody can be prepared by a method disclosed in Japanese Patent Laid-Open No. 3-139293. This preparation can be carried out by a method which involves intraperitoneally injecting PM-1 antibody-producing hybridomas BALB/c mice to obtain ascitic fluid, from which the PM-1 antibody is purified, or a method which involves culturing the hybridomas in an appropriate medium, for example, an RPMI1640 medium containing 10% fetal calf serum and 5% BM-Condimed H1 (manufactured by Boehringer Mannheim), a Hybridoma SFM medium (manufactured by Gibco BRL/Life Technologies, Inc.), or a PFHM-II medium (manufactured by Gibco BRL/Life Technologies, Inc.) and purifying the PM-1 antibody from the culture supernatant.

In the present invention, a recombinant antibody produced by use of a gene recombination technique which involves cloning an antibody gene from hybridomas, incorporating the antibody gene into an appropriate vector, and transferring this vector to a host can be used as the monoclonal antibody (see e.g., Borrebaeck C. A. K. and Larrick J. W. THERAPEUTIC MONOCLONAL ANTIBODIES, Published in the United Kingdom by MACMILLAN PUBLISHERS LTD, 1990).

Specifically, mRNAs encoding the variable (V) regions of the antibody are isolated from cells, for example, hybridomas, producing the antibody of interest. For the mRNA isolation, total RNA is prepared by a method known in the art, for example, a guanidine ultracentrifugation method (Chirgwin, J. M. et al., Biochemistry (1979) 18, 5294-5299) or an AGPC method (Chomczynski, P. et al., Anal. Biochem. (1987) 162, 156-159), and the mRNAs are prepared using mRNA Purification Kit (manufactured by Pharmacia Corp.) or the like. Alternatively, the mRNAs can be directly prepared by use of QuickPrep mRNA Purification Kit (manufactured by Pharmacia Corp.).

Antibody V region cDNAs are synthesized from the obtained mRNAs using reverse transcriptase. The cDNA synthesis can be carried out using AMV Reverse Transcriptase First-strand cDNA Synthesis Kit or the like. Also, 5'-Ampli FINDER RACE Kit (manufactured by Clontech Laboratories, Inc.) and a PCR-based 5'-RACE method (Frohman, M. A. et al., Proc. Natl. Acad. Sci. USA (1988) 85, 8998-9002; and Belyavsky, A. et al., Nucleic Acids Res. (1989) 17, 2919-2932) can be used in the cDNA synthesis and amplification. The DNA fragments of interest are purified from the obtained PCR products and ligated with vector DNAs. Recombinant vectors are thereby prepared and transferred to E. coli or the like. Colonies are selected to prepare desired recombinant vectors. The nucleotide sequences of the DNAs of interest are confirmed by a method known in the art, for example, a deoxy method.

If DNAs encoding the V regions of the antibody of interest are obtained, these DNAs are linked to DNAs encoding constant regions (C regions) of a desired antibody, and these linked DNAs are incorporated into expression vectors. Alternatively, the DNAs encoding the antibody V regions may be incorporated into expression vectors containing the DNAs of the antibody C regions.

For the production of the antibody used in the present invention, the antibody gene is incorporated into an expression vector such that the antibody gene is expressed under the control of expression control regions, for example, an enhancer and a promoter, as mentioned later. Next, host cells are transformed with this expression vector, and the antibody can be expressed.

In the present invention, a gene recombinant antibody that has been artificially engineered for the purpose of, for example, reducing the heterologous antigenicity against humans, for example, a chimeric antibody or a humanized antibody, can be used. Such an engineered antibody can be produced by use of a known method.

The chimeric antibody is obtained by linking the antibody V region-encoding DNAs obtained as described above to human antibody C region-encoding DNAs, and incorporating the linked DNAs into expression vectors, which are then transferred to a host, followed by the production of the antibody (see European Patent Application Publication No. EP125023 and International Publication No. WO92-19759). A chimeric antibody useful in the present invention can be obtained by use of this known method.

The humanized antibody, also called reshaped human antibody, is obtained by grafting the complementarity-determining regions (CDRs) of a non-human mammalian antibody, for example, a mouse antibody, to the complementarity-determining regions of a human antibody. A general gene recombination approach therefor is also known (see European Patent Application Publication No. EP125023 and International Publication No. WO92-19759).

Specifically, DNA sequences designed so as to link mouse antibody CDRs and human antibody framework regions (FRs) are synthesized by PCR using several prepared oligonucleotides having terminal portions overlapping with each other. The obtained DNAs are linked to DNAs encoding human antibody C regions. Subsequently, the linked DNAs are incorporated into expression vectors, which are then transferred to a host, followed by the production of the antibody to obtain the humanized antibody (see European Patent Application Publication No. EP239400 and International Publication No. WO92-19759).

The human antibody FRs to be connected via CDRs are selected such that the complementarity-determining regions form a favorable antigen-binding site. If necessary, amino acids in the framework regions of the antibody variable regions may be substituted such that the complementarity-determining regions of the resulting reshaped human antibody form an appropriate antigen-binding site (Sato, K. et al., Cancer Res. (1993) 53, 851-856).

Usually, human antibody C regions are used for the chimeric antibody or the humanized antibody. Examples of the human antibody heavy chain C region include Cγ. For example, Cγ1, Cγ2, Cγ3, or Cγ4 can be used. Examples of the human antibody light chain C region can include κ and X. These human antibody C regions may be modified in order to improve the stability of the antibody or the stability of production thereof.

The chimeric antibody is composed of the variable regions of a non-human mammal-derived antibody and human antibody-derived C regions. The humanized antibody is composed of the complementarity-determining regions of a non-human mammal-derived antibody and human antibody-derived framework regions and C regions. These antibodies exhibit reduced antigenicity in human bodies and as such, are useful as antibodies for use as drugs.

Specific examples of the humanized antibody used in the present invention include humanized PM-1 antibodies (see International Publication No. WO92-19759).

In addition to the aforementioned methods for obtaining a human antibody, a technique of obtaining a human antibody by panning using a human antibody library is also known. For example, human antibody variable regions are expressed as a single-chain antibody (scFv) on the surface of phages by a phage display method, and a phage binding to the antigen may be selected. The gene of the selected phage can be analyzed to determine DNA sequences encoding the variable regions of the human antibody binding to the antigen. If the DNA sequence of scFv binding to the antigen is revealed, an appropriate expression vector containing this sequence can be prepared to obtain the human antibody. These methods have already been well known. See WO92/01047, WO92/20791, WO93/06213, WO93/11236, WO93/19172, WO95/01438, and WO95/15388.

The antibody gene constructed as described above can be expressed by a method known in the art. In the case of using mammalian cells, the antibody gene can be expressed by use of a DNA in which a useful promoter routinely used, the antibody gene to be expressed, and a poly-A signal 3'-downstream thereof are functionally linked, or a vector containing the DNA. Examples of the promoter/enhancer can include human cytomegalovirus immediate early promoter/enhancer.

Alternatively, a promoter/enhancer of a virus such as retrovirus, polyoma virus, adenovirus, or simian virus 40 (SV40), a mammalian cell-derived promoter/enhancer such as human elongation factor 1α (HEF1α), or the like can be used as the promoter/enhancer for the antibody expression used in the present invention.

In the case of using, for example, the SV40 promoter/enhancer, the antibody expression can be readily carried out according to the method of Mulligan et al. (Mulligan, R. C. et al., Nature (1979) 277, 108-114). In the case of using the HEF1α promoter/enhancer, the antibody expression can be readily carried out according to the method of Mizushima et al. (Mizushima, S. and Nagata, S. Nucleic Acids Res. (1990) 18, 5322).

In the case of using prokaryotic cells as the host, bacterial cells can be used in the production system. *E. coli* or *Bacillus subtilis* is known as the bacterial cells.

For *E. Coli*, a useful promoter routinely used, a signal sequence for antibody secretion, and the antibody gene to be expressed can be functionally linked and expressed. Examples of the promoter can include lacZ promoter and araB promoter. In the case of using the lacZ promoter, the antibody expression can be carried out according to the method of Ward et al. (Ward, E. S. et al., Nature (1989) 341, 544-546; and Ward, E. S. et al. FASEB J. (1992) 6, 2422-2427). In the case of using the araB promoter, the antibody expression can be carried out according to the method of Better et al. (Better, M. et al. Science (1988) 240, 1041-1043).

In the case of production in the periplasm of *E. coli*, pelB signal sequence (Lei, S. P. et al., J. Bacteriol. (1987) 169, 4379-4383) can be used as the signal sequence for antibody secretion. The antibody produced in the periplasm is separated and then used after appropriate refolding of the antibody structure (see e.g., WO96/30394).

A replication origin derived from SV40, polyoma virus, adenovirus, bovine papillomavirus (BPV), or the like can be used. The expression vector can contain a selective marker such as aminoglycoside phosphotransferase (APH) gene, thymidine kinase (TK) gene, *E. coli* xanthine guanine phosphoribosyltransferase (Ecogpt) gene, or dihydrofolate reductase (dhfr) gene in order to increase the number of gene copies in the host cell system.

For the production of the antibody used in the present invention, an arbitrary production system can be used. The production system for the antibody production is any of in vitro and in vivo production systems. Examples of the in vitro production system include a production system using eukaryotic cells and a production system using prokaryotic cells.

In the case of using eukaryotic cells as the host, animal cells, plant cells, or fungal cells can be used in the production system. (1) Mammalian cells, for example, CHO, COS, myeloma, BHK (baby hamster kidney), HeLa, and Vero, (2) amphibian cells, for example, *Xenopus* oocytes, or (3) insect cells, for example, sf9, sf21, and Tn5 are known as the animal cells. *Nicotiana tabacum*-derived cells are known as the plant cells and can be callus-cultured. Yeasts of, for example, the genus *Saccharomyces* (e.g., *Saccharomyces cerevisiae*) or filamentous fungi of, for example, the genus *Aspergillus* (e.g., *Aspergillus niger*) are known as the fungal cells.

The antibody gene of interest is transferred to these cells by transformation, and the transformed cells are cultured in vitro to obtain the antibody. This culture is carried out according to a method known in the art. For example, DMEM, MEM, RPMI1640, or IMDM can be used as a medium and may be used in combination with a serum supplement such as fetal calf serum (FCS). Alternatively, the cells thus harboring the antibody gene may be transferred to the peritoneal cavity or the like of an animal so that the antibody is produced in vivo.

On the other hand, examples of the in vivo production system include a production system using an animal and a production system using a plant. In the case of using the animal, a mammal, an insect, or the like can be used in the production system.

A goat, a pig, sheep, a mouse, cattle, or the like can be used as the mammal (Vicki Glaser, SPECTRUM Biotechnology Applications, 1993). A silkworm can be used as the insect. In the case of using the plant, for example, tobacco can be used.

The antibody gene is transferred to such an animal or a plant, and the antibody is produced in the body of the animal or the plant and recovered. For example, the antibody gene is prepared as a fusion gene by insertion in frame into a gene encoding a protein specifically produced in milk, such as goat β casein. A DNA fragment having the fusion gene of the inserted antibody gene is injected into a goat embryo, and this embryo is introduced into a female goat. The desired antibody is obtained from milk produced by a transgenic goat born from the embryo-recipient goat, or progeny thereof. Hormone may be appropriately used for the transgenic goat in order to increase the amount of the milk containing the desired antibody produced by the transgenic goat (Ebert, K. M. et al., Bio/Technology (1994) 12, 699-702).

In the case of using the silkworm, the silkworm is infected with baculovirus having an insert of the antibody gene of interest, and the desired antibody is obtained from the body fluid of this silkworm (Maeda, S. et al., Nature (1985) 315, 592-594). In the case of using the tobacco, the antibody gene of interest is inserted to a vector for expression in plants, for example, pMON530, and this vector is transferred to a bacterium such as *Agrobacterium tumefaciens*. Tobacco, for example, *Nicotiana tabacum*, is infected with this bacterium, and the desired antibody is obtained from the leaf of this tobacco (Julian, K.-C. Ma et al., Eur. J. Immunol. (1994) 24, 131-138).

In the case of producing the antibody in the in vitro or in vivo production system as mentioned above, an antibody heavy chain (H chain)-encoding DNA and an antibody light chain (L chain)-encoding DNA may be incorporated into separate expression vectors, and the host can be co-transformed with these expression vectors. Alternatively, the H chain-encoding DNA and the L chain-encoding DNA may be incorporated into a single expression vector, and the host can be transformed with this expression vector (see International Publication No. WO94-11523).

The antibody used in the present invention may be a fragment of the antibody or a modified form of the antibody as long as the fragment or the modified form can be suitably used in the present invention. Examples of the antibody fragment include Fab, F(ab')2, Fv, and single-chain Fv (scFv) containing H and L chain Fvs linked through an appropriate linker.

Specifically, the antibody fragment is formed by the treatment of the antibody with an enzyme, for example, papain or pepsin, or is expressed in appropriate host cells after construction of a gene encoding the antibody fragment and subsequent transfer of this gene to an expression vector (see e.g., Co, M. S. et al., J. Immunol. (1994) 152, 2968-2976; Better, M. & Horwitz, A. H. Methods in Enzymology (1989) 178, 476-496; Plueckthun, A. & Skerra, A. Methods in Enzymology (1989) 178, 497-515; Lamoyi, E., Methods in Enzymology (1989) 121, 652-663; Rousseaux, J. et al., Methods in Enzymology (1989) 121, 663-66; and Bird, R. E. et al., TIBTECH (1991) 9, 132-137).

The scFv is obtained by linking the H chain V region and the L chain V region of the antibody. In this scFv, the H chain V region and the L chain V region are linked via a linker, preferably a peptide linker (Huston, J. S. et al., Proc. Natl. Acad. Sci. U.S.A. (1988) 85, 5879-5883). The H chain V region and the L chain V region in the scFv may be derived from any of those described above as the antibody according to the present invention. For example, an arbitrary single-chain peptide composed of 12 to 19 amino acid residues is used as the peptide linker for linking the V regions.

A DNA encoding the scFv is obtained by using a DNA encoding the antibody H chain or the H chain V region and a DNA encoding the antibody L chain or the L chain V region as templates to amplify each DNA moiety encoding the desired amino acid sequence, of these sequences, by PCR using a primer pair annealing to both ends thereof, followed by amplification by the combined use of a DNA encoding the peptide linker moiety and a primer pair annealing thereto such that the both ends of the peptide linker are linked to the H chain and the L chain, respectively.

Once the scFv-encoding DNA is prepared, an expression vector containing the DNA, and a host transformed with the expression vector can be obtained according to routine methods. Also, the scFv can be obtained according to a routine method using the host.

These antibody fragments can be expressed through the obtainment of their genes in the same way as above and produced by the host. The "antibody" according to the present invention also encompasses these antibody fragments.

Antibodies bound with various molecules such as polyethylene glycol (PEG) may be used as the modified form of the antibody. The "antibody" according to the present invention also encompasses these modified forms of the antibody. Such a modified form of the antibody can be obtained by the chemical modification of the obtained antibody. These methods have already been established in the art.

The antibody produced and expressed as described above can be separated from the inside or outside of the cells or from the host and purified until homogeneous. The separation and purification of the antibody used in the present invention can be carried out by affinity chromatography. Examples of columns for use in the affinity chromatography include protein A columns and protein G columns. Examples of carriers for use in the protein A columns include Hyper D, POROS, and Sepharose F.F. Any of other ordinary separation and purification methods for use in proteins can be used without limitations.

The antibody used in the present invention can be separated and purified by appropriately selecting or combining, for example, chromatography other than the affinity chromatography, filters, ultrafiltration, salting out, and/or dialysis. Examples of the chromatography include ion-exchange chromatography, hydrophobic chromatography, and gel filtration. These chromatography techniques are applicable to HPLC (high-performance liquid chromatography). Alternatively, reverse-phase HPLC may be used.

The concentration of the antibody thus obtained can be measured by, for example, absorbance measurement or ELISA. Specifically, in the case of measuring the concentration by the absorbance measurement, the absorbance is measured at 280 nm after appropriate dilution of the antibody with PBS(−), and the concentration is calculated with 1 mg/ml as 1.35 OD. Alternatively, the concentration can be measured by ELISA as follows: goat anti-human IgG (manufactured by TAG) diluted to 1 µg/ml with a 0.1 M bicarbonate buffer solution (pH 9.6) is added at 100 µl/well to a 96-well plate (manufactured by Nunc/Thermo Fisher Scientific, Inc.) and incubated overnight at 4° C. to immobilize the antibody thereon. After blocking, an appropriately diluted antibody used in the present invention or a sample containing the antibody, or a preparation human IgG (manufactured by Cappel Laboratories, Inc.) is added thereto at 100 µl/well and incubated at room temperature for 1 hour. After washing, alkaline phosphatase-labeled anti-human IgG (manufactured by BioSource International, Inc.) diluted 5000-fold is added thereto at 100 µl/well and incubated at room temperature for 1 hour. After washing, a substrate solution is added thereto and incubated. Then, the absorbance is measured at 405 nm using MICROPLATE READER Model 3550 (manufactured by Bio-Rad Laboratories, Inc.) to calculate the concentration of the antibody of interest.

Specific examples of the anti-IL-6 antibody can include, but are not particularly limited to, MH166 (Matsuda, T. et al., Eur. J. Immunol. (1998) 18, 951-956) and SK2 antibody (Sato K et al., Academic proceedings of the 21st General Meeting of the Japanese Society for Immunology (1991) 21, 166).

Specific examples of the anti-IL-6 receptor antibody include, but are not particularly limited to, MR16-1 antibody (Tamura, T. et al. Proc. Natl. Acad. Sci. USA (1993) 90, 11924-11928), PM-1 antibody (Hirata, Y. et al., J. Immunol. (1989) 143, 2900-2906), AUK12-20 antibody, AUK64-7 antibody, and AUK146-15 antibody (International Publication No. WO92-19759). Among them, preferred examples of the monoclonal antibody against the human IL-6 receptor include, but are not limited to, the PM-1 antibody, and preferred examples of the monoclonal antibody against the mouse IL-6 receptor include, but are not limited to, the MR16-1 antibody. Preferred examples of the humanized anti-IL-6 receptor antibody can include a humanized PM-1 antibody (Tocilizumab, MRA). Other preferred examples of the humanized anti-IL-6 receptor antibody can include antibodies described in WO2009/041621 and WO2010/035769. Examples of other preferred forms of the anti-IL-6 receptor antibody can include an anti-IL-6 receptor antibody that recognizes the same epitope as that recognized by the humanized PM-1 antibody (Tocilizumab, MRA).

Specific examples of the anti-gp130 antibody include, but are not particularly limited to, AM64 antibody (Japanese Patent Laid-Open No. 3-219894), 4B11 antibody, 2H4 antibody (U.S. Pat. No. 5,571,513), and B-P8 antibody (Japanese Patent Laid-Open No. 8-291199).

The IL-6 variant used in the present invention is a substance that has binding activity against the IL-6 receptor and does not transduce the biological activity of IL-6. Specifically, the IL-6 variant competes with IL-6 for binding to the IL-6 receptor, but blocks the signal transduction of IL-6 because of not transducing the biological activity of IL-6.

The IL-6 variant is prepared by introducing a variation in IL-6 through the substitution of amino acid residues in the amino acid sequence of IL-6. The origin of IL-6 on which the IL-6 variant is based is not limited and is preferably human IL-6 in consideration of antigenicity, etc. Specifically, the secondary structure of the amino acid sequence of IL-6 is predicted by use of a molecular modeling program known in the art, for example, WHATIF (Vriend et al., J. Mol. Graphics (1990) 8, 52-56), and the influence of the amino acid residues to be substituted on the whole amino acid sequence is evaluated. After determination of appropriate amino acid residues to be substituted, a vector containing a nucleotide sequence encoding the human IL-6 gene is used as a template, and the variation is introduced by usually performed PCR such that the amino acids are substituted to obtain a gene encoding the IL-6 variant. This gene is incorporated into an appropriate expression vector according to the need, and the IL-6 variant can be obtained according to the aforementioned expression, production, and purification methods for the recombinant antibody.

Specific examples of the IL-6 variant can include IL-6 variants disclosed in Brakenhoff et al., J. Biol. Chem. (1994) 269, 86-93, Savino et al., EMBO J. (1994) 13, 1357-1367, WO96-18648, and WO96-17869.

The partial IL-6 receptor peptide is a peptide having a portion or the whole of the amino acid sequence of a region involved in the binding of the IL-6 receptor to IL-6 in the amino acid sequence of the IL-6 receptor. Such a peptide is composed of usually 10 to 80, preferably 20 to 50, more preferably 20 to 40 amino acid residues.

The partial IL-6 receptor peptide can be prepared by identifying the region involved in the binding of the IL-6 receptor to IL-6 in the amino acid sequence of the IL-6 receptor and producing the peptide by a conventionally known method, for example, a genetic engineering approach or a peptide synthesis method on the basis of a portion or the whole of the amino acid sequence of the identified region.

For the preparation of the partial IL-6 receptor peptide by the genetic engineering approach, a DNA sequence encoding the desired peptide is incorporated into an expression vector, and the partial IL-6 receptor peptide can be obtained according to the aforementioned expression, production, and purification methods for the recombinant antibody.

For the preparation of the partial IL-6 receptor peptide by the peptide synthesis method, a method usually used in peptide synthesis, for example, a solid-phase synthesis method or a liquid-phase synthesis method can be used.

Specifically, the peptide synthesis can be carried out according to methods described in Zoku Iyakuhin no Kaihatsu (Development of Pharmaceuticals, Second Series, in English), Vol. 14, Peptide Synthesis, edited by Haruaki Yajima, Hirokawa Shoten Co., Ltd. (1991). The solid-phase synthesis method used is a method which involves, for example, coupling an amino acid corresponding to the C terminus of the peptide to be synthesized to a support insoluble in an organic solvent, and elongating a peptide chain by alternately repeating the reaction of condensing one by one amino acids (their α-amino groups and side chain functional groups have been protected with appropriate protective groups) in a direction from the C terminus toward the N terminus and the reaction of eliminating the protective groups of the α-amino groups of the amino acids or peptide bound onto the resin. The solid-phase peptide synthesis method is broadly divided into Boc and Fmoc methods depending on the types of the protective groups used.

After such synthesis of the peptide of interest, deprotection reaction and cleavage reaction of the peptide chain from the support are carried out. In the cleavage reaction of the peptide chain, usually, hydrogen fluoride or trifluoromethanesulfonic acid can be used for the Boc method, and TFA can be used for the Fmoc method. In the Boc method, the protected peptide resin is treated, for example, in the presence of anisole in hydrogen fluoride. Subsequently, protective group elimination and cleavage from the support are carried out to recover the peptide. This peptide is freeze-dried to obtain a crude peptide. On the other hand, in the Fmoc method, deprotection reaction and cleavage reaction of the peptide chain from the support can be carried out by the same operation as above, for example, in TFA.

The obtained crude peptide can be separated and purified by application to HPLC. The peptide can be eluted under the optimum conditions by use of a water-acetonitrile mixed solvent usually used in protein purification. A fraction corresponding to a peak in the obtained profile of chromatography is separated and then freeze-dried. The peptide fraction thus purified is identified by, for example, mass spectrometric molecular weight analysis, amino acid composition analysis, or amino acid sequence analysis.

The present inventors have further found that PB derived from relapsing-remitting multiple sclerosis patients having a high amount of PB in peripheral blood exhibits high sensitivity to IL-6 and survives in a manner dependent on IL-6. This finding implies that the survival of PB is suppressed by the inhibition of IL-6R expressed on PB. Thus, the present invention relates to a PB growth inhibitor comprising an IL-6 inhibitor as an active ingredient. The present invention also relates to a therapeutic agent for relapsing-remitting multiple sclerosis, comprising an IL-6 inhibitor as an active ingredient. The relapsing-remitting multiple sclerosis is preferably relapsing-remitting multiple sclerosis highly expressing a plasmablast. The "relapsing-remitting multiple sclerosis highly expressing a plasmablast" according to the present invention refers to multiple sclerosis in which a "high amount of a plasmablast (PB)" has been determined in a multiple sclerosis patient. Alternatively, the present invention relates to a therapeutic agent for relapsing-remitting multiple sclerosis which is directed to administration to a relapsing-remitting multiple sclerosis patient having a high amount of PB in peripheral blood, the therapeutic agent comprising an IL-6 inhibitor as an active ingredient.

In the present invention, the phrase "comprising as an active ingredient" means comprising the IL-6 inhibitor as at least one active ingredient and does not limit the content thereof. The growth inhibitor or the therapeutic agent of the present invention may also contain an additional active ingredient other than the IL-6 inhibitor. The therapeutic agent of the present invention may be used not only for therapeutic purposes but for preventive purposes.

The growth inhibitor or the therapeutic agent of the present invention can be formulated according to a routine method (e.g., Remington's Pharmaceutical Science, latest edition, Mark Publishing Company, Easton, U.S.A). The growth inhibitor or the therapeutic agent of the present invention may optionally contain a pharmaceutically acceptable carrier and/or additive. The growth inhibitor or the therapeutic agent of the present invention can contain, for example, a surfactant (PEG, Tween, etc.), an excipient, an antioxidant (ascorbic acid, etc.), a colorant, a flavoring agent, a preservative, a stabilizer, a buffer (phosphate, citrate, other organic acids, etc.), a chelating agent (EDTA, etc.), a suspending agent, a tonicity agent, a binder, a disintegrant, a lubricant, a flowability enhancer, and a corrigent. However, the growth inhibitor or the therapeutic agent of the present invention is not limited by these agents and may appropriately contain other carriers routinely used. Specific examples thereof can include light anhydrous silicic acid, lactose, crystalline cellulose, mannitol, starch, carmellose calcium, carmellose sodium, hydroxypropylcellulose, hydroxypropylmethylcellulose, polyvinylacetal diethylaminoacetate, polyvinylpyrrolidone, gelatin, medium-chain fatty acid triglyceride, polyoxyethylene hydrogenated castor oil 60, saccharose, carboxymethylcellulose, corn starch, and inorganic salts. Also, the growth inhibitor or the therapeutic agent of the present invention may contain other low-molecular-weight polypeptides, proteins (e.g., serum albumin, gelatin, and immunoglobulin), and amino acids. In the case of preparing an aqueous solution for injection, the IL-6 inhibitor is dissolved in, for example, an isotonic solution containing saline, glucose, or other aids. Examples of the aids include D-sorbitol, D-mannose, D-mannitol, and sodium chloride. The solution may be further used in combination with an appropriate solubilizer, for example, an alcohol (ethanol, etc.), a polyalcohol (propylene glycol, PEG, etc.), or a nonionic surfactant (polysorbate 80 or HCO-50).

The IL-6 inhibitor may be enclosed in a microcapsule (microcapsule made of hydroxymethylcellulose, gelatin, poly[methyl methacrylate], or the like) or prepared into a colloid drug delivery system (liposomes, albumin microspheres, microemulsions, nanoparticles, and nanocapsules, etc.) (see e.g., Remington's Pharmaceutical Science 16th edition & Oslo Ed. (1980)). Methods for formulating drugs as sustained-release drugs are also known in the art and may be applied to the interferon beta and the IL-6 inhibitor of the present invention (Langer et al., J. Biomed. Mater. Res. (1981) 15: 167-277; Langer, Chem. Tech. (1982) 12: 98-105; U.S. Pat. No. 3,773,919; European Patent Publication No. EP 58,481; Sidman et al., Biopolymers (1983) 22: 547-56; and EP 133,988). The growth inhibitor or the therapeutic agent of the present invention may be further supplemented or mixed with hyaluronidase to increase the amount of a solution for subcutaneous administration (e.g., WO2004/078140).

The growth inhibitor or the therapeutic agent of the present invention can be administered through any of oral and parenteral routes and is preferably administered parenterally. Specifically, the growth inhibitor or the therapeutic agent of the present invention is administered to a patient through injection or percutaneous administration. Examples of the dosage form of the injection include intravenous injection, intramuscular injection, intraperitoneal injection, and subcutaneous injection, which permit systemic or local administration. The growth inhibitor or the therapeutic agent of the present invention may be injected locally, particularly, intramuscularly, to a treatment site or the neighborhood thereof. Examples of the dosage form of the percutaneous administration include ointments, gels, creams, poultices, and patches, which permit systemic or local administration. The administration method can be appropriately selected according to the age and symptoms of a patient. The dose can be selected, for example, within the range of 0.0001 mg to 100 mg of the active ingredient per kg of body weight per dose. Alternatively, the dose for administration to, for example, a human patient, can be selected within the range of 0.001 to 1000 mg/kg body weight of the active ingredient per patient. The single dose preferably contains, for example, approximately 0.01 to 50 mg/kg body weight of the antibody of the present invention. However, the inhibitor or the therapeutic agent of the present invention is not limited by these doses.

The growth inhibitor or the therapeutic agent of the present invention can be used alone for inhibiting the growth of PB or treating and/or preventing relapsing-remitting multiple sclerosis in a human or an animal. Alternatively, the growth inhibitor or the therapeutic agent of the present invention may be orally administered as a mixture with other ingredients that may be usually used in pharmaceuticals or foods. The growth inhibitor or the therapeutic agent of the present invention can also be used in combination with other compounds, microbes, or the like known to have an inhibitory effect on the growth of PB or a therapeutic and/or preventive effect on relapsing-remitting multiple sclerosis.

The present invention further relates to a method for treating and preventing or for treating or preventing relapsing-remitting multiple sclerosis, comprising the step of administering an IL-6 inhibitor to an animal. The present invention further relates to a method for inhibiting the growth of PB, comprising the step of administering an IL-6 inhibitor to an animal. Examples of the recipient of the IL-6 inhibitor include mammals. Examples of the mammals include humans and non-human mammals in need of the treatment or prevention of arteriosclerosis and preferably include humans and monkeys, more preferably humans.

The present invention further relates to an IL-6 inhibitor for use for inhibiting the growth of PB, and an IL-6 inhibitor for use for treating and preventing or for treating or preventing relapsing-remitting multiple sclerosis. Alternatively, the present invention relates to use of an IL-6 inhibitor in the production of a drug for treating and preventing or for treating or preventing relapsing-remitting multiple sclerosis, or in the production of a PB growth inhibitor.

The present invention further relates to a method for producing a drug for treating and preventing or for treating or preventing relapsing-remitting multiple sclerosis, or a PB growth inhibitor, comprising the step of mixing an IL-6 inhibitor with a pharmaceutically acceptable carrier.

All prior art literatures cited herein are incorporated herein by reference.

EXAMPLES

Next, the present invention will be described further specifically with reference to Examples. However, the present invention is not intended to be limited by Examples below.

[Example 1] Measurement of Amount of Plasmablast

RRMS patients were classified into clinically typical cases (Typical MS: tMS) and atypical cases (Atypical MS: atMS). The atMS group involved the following cases:
case having atypical characteristics as MS proposed by DH Miller et al. (Non Patent Literature 6);
IFN-β-resistant case;
case with skin ulcer associated with treatment with IFN-β;
case with other concomitant immune disorders; and
case having NMO-like characteristics (having lesions localized to the optic nerve and the spinal cord or having a long spinal cord lesion).

On the other hand, the tMS group involved cases free from these characteristics.

As a result, both of the groups were found to have clinical characteristics as shown in Table 1.

TABLE 1

| Clinical backgrounds of subject RRMS patients and healthy persons | | | |
|---|---|---|---|
| | Typical MS | Atypical MS | Healthy donors |
| Number | 14 | 37 | 8 |
| Age | 41.5 ± 11.9 | 40.3 ± 11.9 | 40.3 ± 5.8 |
| Gender (F/M) | 7/7 | 21/16 | 6/2 |
| Duration (y) | 11.9 ± 7.2 | 12.3 ± 11.9 | |
| OCB | 55.6% | 55.6% | |
| Barkhof criteria | 57.1% | 51.3% | |
| LESCLs | 0.0% | 5.4% | |
| DMT | 50.0% | 54.1% | |
| | IFN-b | IFN-b, PSL, TAC, MTX | |

F/M: Female/Male
Duration (y): Disease duration (years)
OCB: Oligoclonal band (proportion of OCB-positive patients)
Barkhof criteria (proportion of patients having brain lesions that satisfied the Barkhof criteria
[Non Patent Literatures 7 and 8])
LESCLs: Longitudinally extensive spinal cord lesions (proportion of patients who exhibited a lesion of the spinal cord equal to or longer than 3 vertebral segments in magnetic resonance imaging (MRI))
DMT: Disease modifying therapy (proportion of patients who had already undergone DMT at the time of blood collection)
IFN-β: Interferon beta
PSL: Prednisolone
TAC: Tacrolimus
MTX: Methotrexate Next, peripheral blood was collected from each of tMS, atMS, and healthy donors (HD) and centrifuged using Ficoll-Paque Plus (GE Healthcare Biosciences Corp.) to separate peripheral blood mononuclear cells (PBMC). The separated PBMC was co-stained with a fluorescent anti-CD3 antibody (anti-CD3-PerCP-Cy5.5: BioLegend, Inc., 300430), a fluorescent anti-CD14 antibody (anti-CD14-APC: BioLegend, Inc., 301808), a fluorescent anti-CD19 antibody (anti-CD19-APC-Cy7, BD Biosciences, 348794), a fluorescent anti-CD27 antibody (anti-CD27-PE-Cy7, BD Biosciences, 560609), a fluorescent anti-CD180 antibody (anti-CD180-PE, BD Biosciences, 551953), and a fluorescent anti-CD38 antibody (anti-CD38-FITC, Beckman Coulter, Inc., A0778) and analyzed by flow cytometry under conditions shown in Table 2 using FACS Canto II (BD Biosciences) to exclude $CD3^+$ T cells or $CD14^+$ monocytes (FIG. 1A). Cells having a CD19 expression level of $10^3$ or higher were defined as $CD19^+$ cells, which were further defined as B cells (FIG. 1B). B cells having a CD27 expression level of $2\times10^3$ or higher are defined as $CD27^+$ cells, and B cells having a CD180 expression level of $2\times10^3$ or lower are defined as $CD180^-$ cells (FIG. 1C). B cells having a CD38 expression level of $3\times10^3$ or higher are defined as $CD38^{high}$ cells. According to these criteria, a $CD19^+CD27^+CD180^-CD38^{high}$ fraction (PB) was obtained. The amount of PB was calculated according to the number of PB/the number of $CD19^+$ B cells×100(%). In FIGS. 1B and 1C, naive B cells ($CD19^+CD27^-$) and memory B cells ($CD19^+CD27^+CD180±$) are also shown as B cell subsets other than PB.

TABLE 2

| Measurement conditions for FACS Canto II | | | |
|---|---|---|---|
| Parameters | Type | Voltage | Log |
| FSC | A, H, W | 275 | Off |
| SSC | A, H, W | 368 | Off |
| FITC | A | 478 | On |
| PerCP-Cy5.5 | A | 549 | On |
| PE | A | 484 | On |
| PE-Cy7 | A | 615 | On |
| APC | A | 577 | On |
| APC-Cy7 | A | 593 | On |
| Threshold Operator: OR | | | |
| Threshold Parameters | | Threshold | |
| FSC | | 5000 | |
| Compensation State: Enabled | | | |
| Fluorochromes | | Value(%) | |
| PerCP-Cy5.5-FITC | | 2.94 | |
| PE-FITC | | 28.66 | |
| PE-Cy7-FITC | | 0.47 | |
| APC-FITC | | 0.00 | |
| APC-Cy7-FITC | | 0.00 | |
| FITC-PerCP-Cy5.5 | | 0.00 | |
| PE PerCP Cy5.5 | | 0.09 | |
| PE-Cy7-Pe-CP-Cy5.5 | | 39.99 | |
| APC PerCP Cy5.5 | | 2.95 | |
| APC-Cy7-PerCP-Cy5.5 | | 9.77 | |
| FITC PE | | 0.94 | |
| PerCP-Cy5.5-PE | | 11.52 | |
| PE Cy7 PE | | 2.41 | |
| APC-PE | | 0.25 | |
| APC-Cy7-PE | | 0.02 | |
| FITC-PE-Cy7 | | 0.03 | |
| PerCP Cy5.5 PE Cy7 | | 1.66 | |
| PE-PE-Cy7 | | 0.59 | |
| APC-PE-Cy7 | | 0.05 | |
| APC-Cy7-PE-Cy7 | | 9.24 | |
| FITC-APC | | 0.59 | |
| PerCP-Cy5.5-APC | | 4.97 | |
| PE-APC | | 1.84 | |
| PE-Cy7-APC | | 2.41 | |
| APC-Cy7-APC | | 17.22 | |
| FITC APC Cy7 | | 0.00 | |
| PerCP Cy5.5 APC Cy7 | | 0.00 | |
| PE-APC-Cy7 | | 0.27 | |
| PF-Cy7-APC-Cy7 | | 1.87 | |
| APC-APC-Cy7 | | 4.43 | |

Figure 2A:
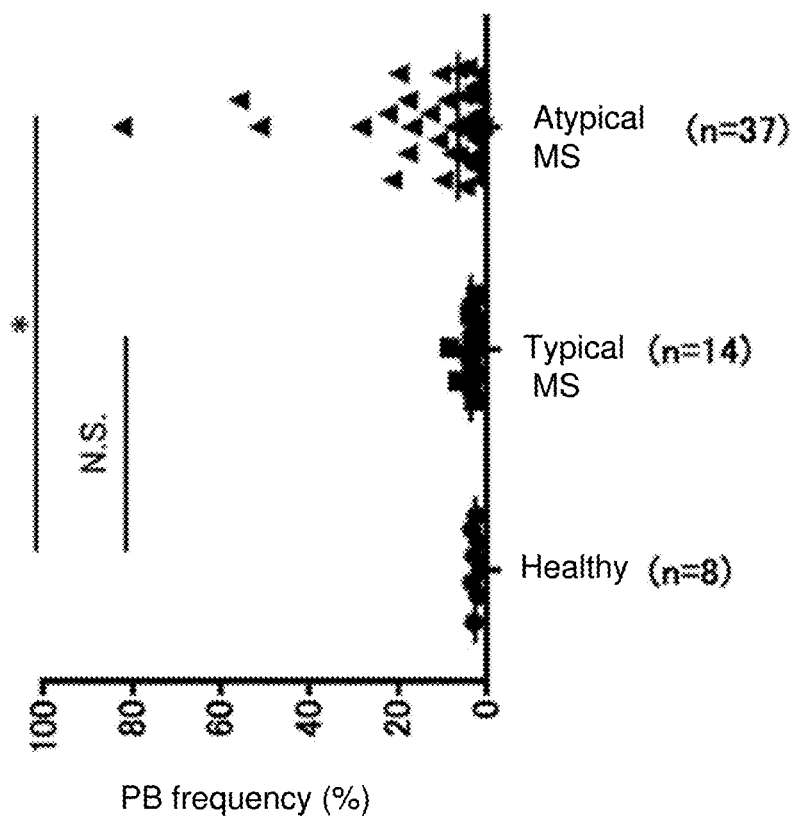
FIG. 2A shows the distribution for all subjects.

The results of measuring the amount of PB are shown in FIG. 2. FIG. 2A shows results of comparing the amount of PB in peripheral blood (PB frequency) among the RRMS patient groups (n=51) classified into typical cases (Typical MS, n=14) and atypical cases (Atypical MS, n=37) and healthy persons (Healthy, n=8). FIG. 2B shows results of comparing the amount of PB for subjects with untreated RRMS among the RRMS cohort analyzed in FIG. 2A. The horizontal line within the scatter diagram represents the median value (* P<0.05 (by Kruskal Wallis test with Dunn's post hoc test); N.S.: not significant statistically).

Both for all of the test subjects and for the untreated subjects, only atMS was shown to have a high amount of a plasmablast (PB). Since patients low responsive to treatment with IFN-β are included in atMS according to the definitions, these patients are suggested to be identifiable on the basis of the amount of PB.

[Example 2] Relationship Between Amount of PB in Peripheral Blood and Treatment with IFN-β

Figure 3:
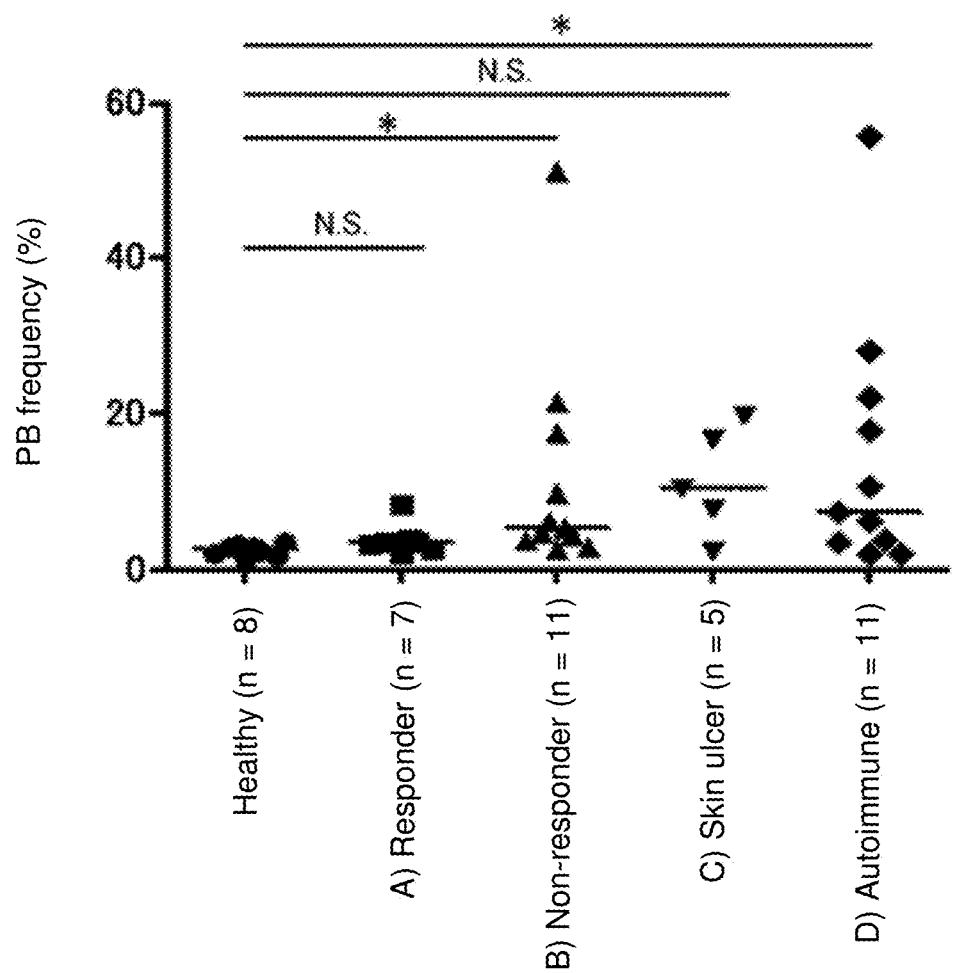
FIG. 3 is a diagram showing the distribution of the amount of PB in RRMS subgroups and a healthy individual group.

The amount of PB in subgroups of RRMS patients was compared (FIG. 3). Specifically, the RRMS patients were classified into 4 subgroups according to conditions based on suitability for IFN-β, and each subgroup was compared with healthy persons (Healthy (n=8)) in terms of the amount of PB in peripheral blood. These 4 subgroups were as follows:
A) Responder: Responsive group (a group confirmed to receive the good therapeutic effect and be suitable for the treatment; n=7)
B) Non-responder: Resistant group (a group confirmed to receive the poor therapeutic effect or confirmed to be not suitable for the treatment due to aggravation; n=11)
C) Skin ulcer: Skin ulcer group (a group confirmed to be not suitable for the treatment with IFN-β because skin ulcer was induced; n=5)
D) Autoimmune: Group with concomitant immune disorder (a group confirmed to be not suitable for IFN-β because of having concomitant immune disorder centering on an autoimmune disorder; n=11).

As shown in FIG. 3, the amount of PB was low in the healthy individuals and the group A, whereas the amount of PB was high in the groups B to D. This demonstrated that the therapeutic effect of IFN-β on RRMS can be predicted to be low for highly PB-expressing patients by measuring the amount of PB in peripheral blood (PB frequency: Amount of PB; the horizontal line represents the median value (* P<0.05 (by Kruskal-Wallis test with Dunn's post hoc test); N.S.: not significant statistically)).

[Example 3] Expression of IL-6 Receptor (IL-6R) in RRMS-Derived PB

Figure 4C:
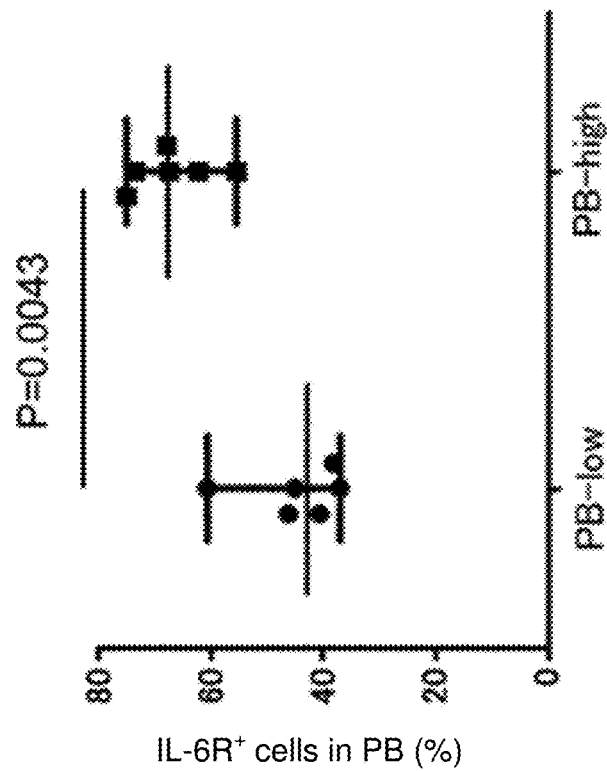
FIG. 4C shows the comparison of the ratio of IL-6R-expressing cells between PB derived from RRMS having a low amount of PB in peripheral blood (PB-low MS) and PB derived from RRMS having a high amount of PB in peripheral blood (PB-high MS).
Figure 4B:
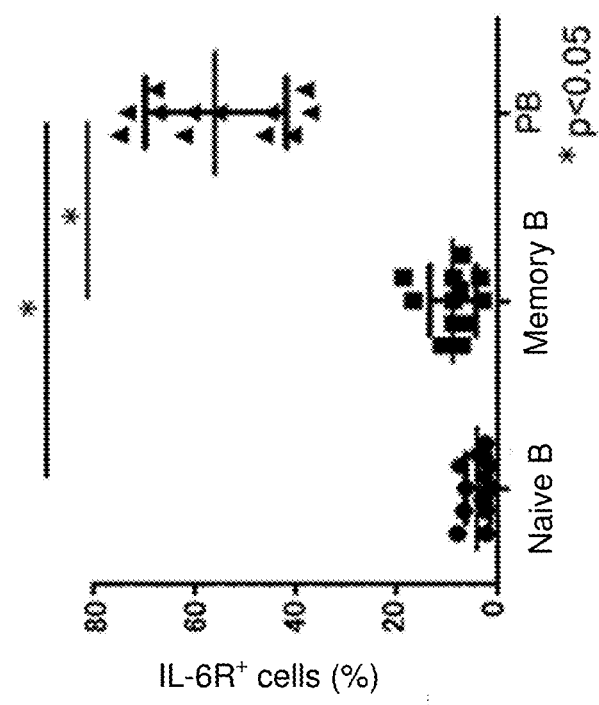
FIG. 4B shows the comparison of the ratio of IL-6R-expressing cells among B cell subsets (naive B cells, memory B cells, and PB).

The expression of IL-6R in the peripheral blood of RRMS patients (n=12) was compared among B cell subsets (naive B cells, memory B cells, and PB). Specifically, PBMC of each of the RRMS patients (n=12) was reacted with an anti-IL-6R antibody (isotype: mouse IgG1). Then, anti-IL-6R antibody-positive cells were labeled by the addition of a fluorescent secondary antibody (anti-mouse IgG1). Then, the cells were co-stained with a fluorescent anti-CD19, -CD27, -CD38, and -CD180 antibodies and analyzed by flow cytometry. Staining was also carried out by using purified mouse IgG1 as an isotype control for the experimental groups using the anti-IL-6R antibody. The frequency of IL-6R expressing cell was compared among the B cell subsets. The B cell subsets were defined as follows:
Naive B cell: $CD19^+CD27^-$
Memory B cell: $CD19^+CD27^+CD180^+$
Plasmablast (PB): $CD19^+CD27^+CD180^-CD38^{high}$ As a result, PB was found to have a very high expression level of IL-6R (FIGS. 4A and 4B). FIG. 4A shows a typical histogram as to IL-6R expression in the B cell subsets. The upper diagrams depict control data obtained using the isotype control antibody, and the lower diagrams depict experimental group data obtained using the anti-IL-6R antibody. The number represents the frequency of IL-6R-positive cells. The frequency of IL-6R-positive cells was high in PB compared with naive B cells and memory B cells. In FIG. 4B, the frequency of IL-6R-positive cells was compared among the B cell subsets of 12 RRMS subjects by a scatter diagram. $IL-6R^+$ cells (%) represent the frequency of IL-6R-positive cells in each B cell subset. The frequency of IL-6R-positive cells was significantly higher in PB compared with those of the other B cell subsets (* P<0.05 by Kruskal-Wallis test with Dunn's post hoc test). The frequency of IL-6R-positive cells in peripheral blood PB was compared among 12 RRMS cases composed of 6 cases with RRMS having a low amount of PB in peripheral blood (PB-low MS) and 6 cases with RRMS having a high amount of PB in peripheral blood (PB-high MS). As a result, the frequency of IL-6R-positive cells was significantly higher in PB derived from PB-high MS (FIG. 4C, P=0.0043 by Mann-Whitney U-test). In FIG. 4C, $IL-6R^+$ cells in PB (%) represent the frequency of IL-6R-positive cells in PB. The horizontal line within the scatter diagram represents the median value and its range.

These results mean that RRMS-derived PB has high sensitivity to IL-6. In addition, the expression of IL-6R was compared between the peripheral blood PB of RRMS having a low amount of PB in peripheral blood (PB-low MS) and the peripheral blood PB of RRMS having a high amount of PB in peripheral blood (PB-high MS). As a result, the frequency of IL-6R-expressing cells was significantly high in PB derived from PB-high MS (FIG. 4C), suggesting that among the peripheral blood plasmablasts (PB) of RRMS, PB derived from PB-high MS has particularly high sensitivity to IL-6.

[Example 4] Relationship Between RRMS-Derived PB and IL-6

PB was separated from PBMC of each RRMS patient by flow cytometry and then cultured for 2 days in the absence of IL-6 or in the presence of IL-6, and its survival rate was measured. Specifically, PB separated from the peripheral blood of each of RRMS patients (n=12) was cultured for 2 days in a medium (AIM-V(R), Gibco BRL/Life Technologies, Inc.) or a medium containing IL-6 (1 ng/ml) and then stained with PI (propidium iodide). The ratio of living cells was measured by flow cytometry ($PI^-$ cells were determined as living cells).

As a result, significant increase in survival rate in the presence of IL-6 was observed in PB derived from RRMS having a high amount of PB in peripheral blood (PB-high MS) (P<0.05) (FIG. 5). By contrast, no change in survival rate between the presence and absence of IL-6 was observed in PB derived from RRMS having a low amount of PB in peripheral blood (PB-low MS). This indicates the possibility that the survival of PB in PB-high MS depends on IL-6 and the survival of PB is suppressed by an IL-6 inhibitor.

Figure 5A:
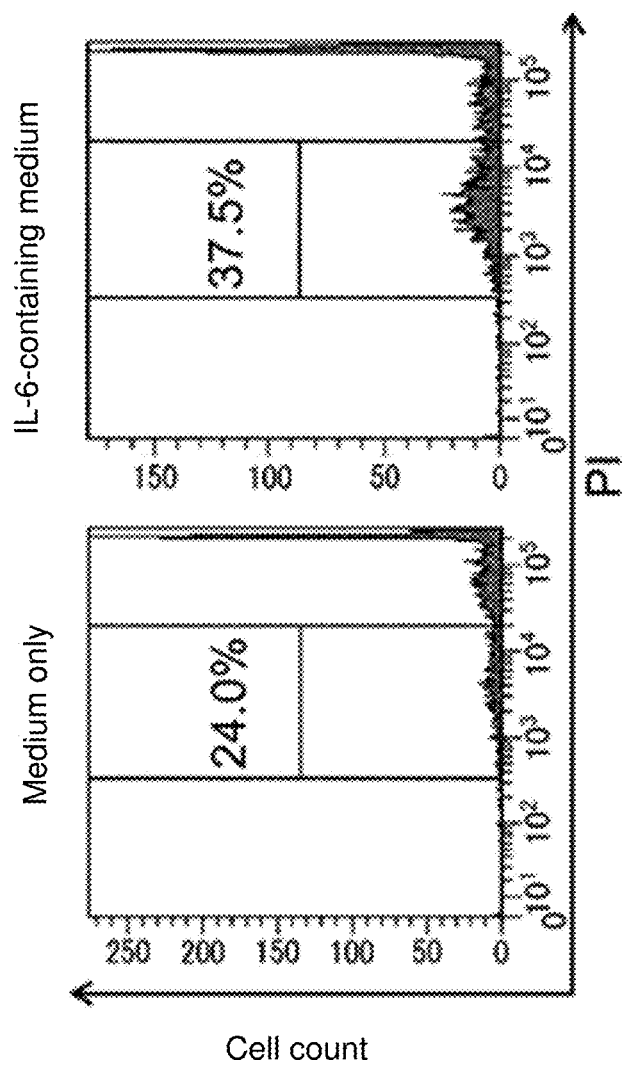
FIG. 5A shows a typical histogram as to the survival rate of RRMS-derived PB, wherein PB was cultured for 2 days in the absence of IL-6 or in the presence of IL-6.

FIG. 5A shows a typical histogram as to the exhibition of PI. $PI^-$ cells were gated, and its ratio was shown (cell count). FIG. 5B shows results of comparing the survival rate between PB in the absence and presence of IL-6 for each case, wherein the measurement values were connected with a line. The RRMS subjects were further classified into subjects with MS having a low amount of PB (PB-low MS) and subjects with MS having a high amount of PB (PB-high MS). Similar comparison was carried out for each group. The results are also shown (Survival rate: the ratio (%) of the number of live PB to the total number of PB).
Medium: Data on PB cultured only in a medium (AIM-V (R))
IL-6: Data on PB cultured in a medium containing 1 ng/ml IL-6
* P<0.05 (by paired t-test)
N.S.: not significant statistically

[Example 5] Effect of Decreasing RRMS-Derived PB by Anti-IL-6 Receptor Antibody

For pretreatment, RRMS patient-derived peripheral blood mononuclear cells (PBMC) were left standing for 20 minutes in the presence of an anti-IL-6 receptor antibody (Tocilizumab for the experiment: 1 ng/ml) or an isotype control antibody (mouse IgG1). The pretreated PBMC was cultured in a medium containing inactivated serum of each patient diluted to 20% by the addition of a solvent (AIM-V(R), Gibco BRL/Life Technologies, Inc.). After 2 days, the amount of PB was measured by flow cytometry.

Figure 6A:
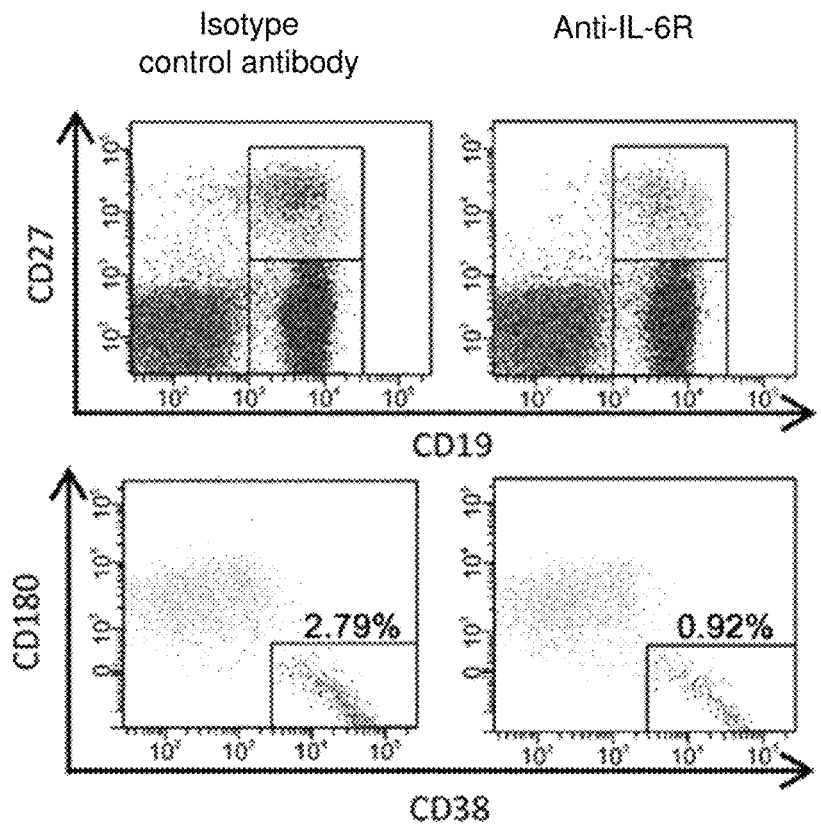
FIG. 6A shows a typical dot plot obtained by flow cytometry in the present Examples. The left and right columns show data after pretreatment with an isotype control antibody and the anti-IL-6 receptor antibody, respectively. The percentage in the plot represents the amount of PB.
Figure 6B:
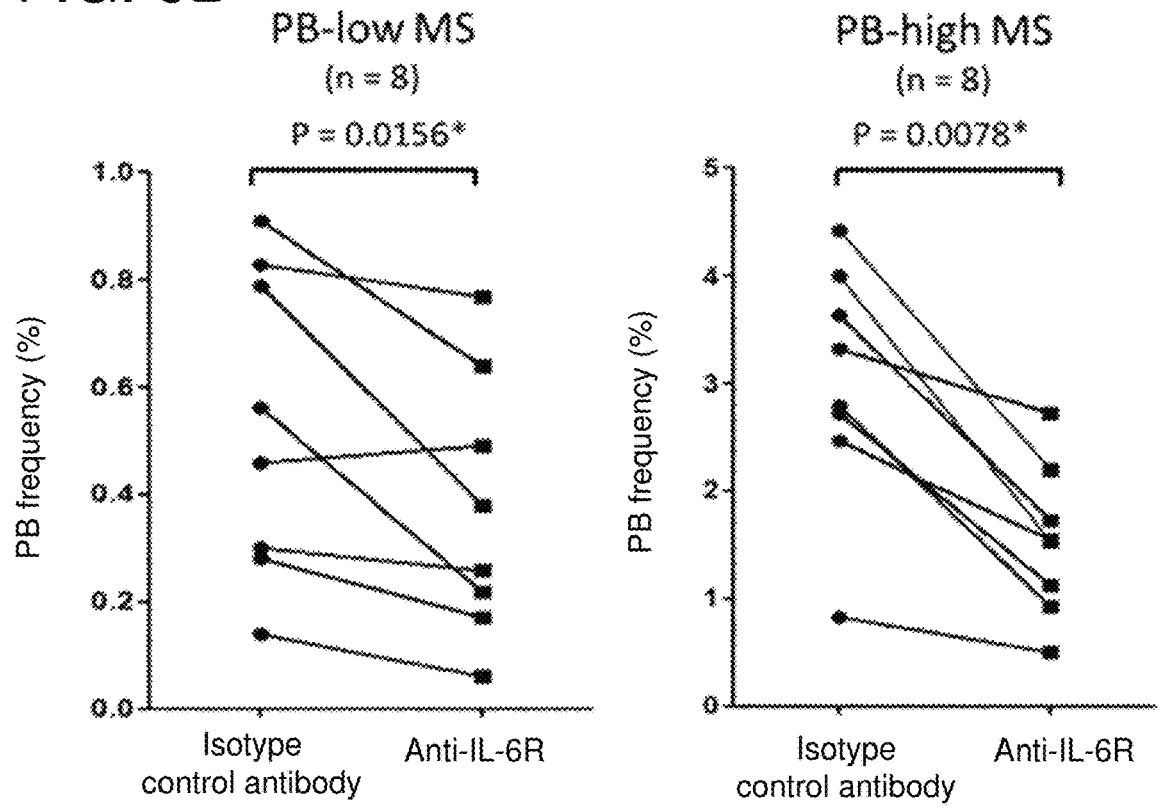
FIG. 6B shows the comparison of the amount of PB after pretreatment with an isotype control antibody or the anti-IL-6 receptor antibody between PB-low MS (n=8) and PB-high MS (n=8). Measurement values obtained for the same patient after the pretreatment with an isotype control antibody or the anti-IL-6 receptor antibody were connected with a line. PB frequency (%): Amount of PB. *P<0.05 by Wilcoxon signed-rank test.

As a result, the amount of PB was found to be significantly decreased after the pretreatment with the anti-IL-6 receptor antibody for both of RRMS having a low amount of PB in peripheral blood (PB-low MS) and RRMS having a high amount of PB in peripheral blood (PB-high MS) (FIG. 6). Change in the scale of the amount of PB after the pretreatment with the anti-IL-6 receptor antibody (the amount of PB after the pretreatment with the anti-IL-6 receptor antibody/the amount of PB after the pretreatment with the isotype control antibody) exhibited a low tendency in PB-high MS (mean±SD: 0.5213±0.1591) compared with PB-low MS (mean±SD: 0.6850±0.2514). In this Example, IL-6 dependency was observed not only for the survival of PB derived from PB-high MS but for the survival of PB derived from PB-low MS. However, the tendency was marked in PB-high MS, suggesting the possibility that PB derived from PB-high MS can be efficiently decreased by the administration of the anti-IL-6 receptor antibody.

INDUSTRIAL APPLICABILITY

According to the present invention, the amount of PB in a sample of a RRMS patient can be measured, thereby predicting the therapeutic effect of IFN-β thereon. Specifically, a RRMS case for which the continuous administration of IFN-β is difficult due to the manifestation of a serious adverse reaction or concomitant immune disorder caused by the administered IFN-β can be predicted. As a result, the present invention allows the avoidance of administration of IFN-β to a patient who cannot be expected to receive the therapeutic effect of administered IFN-β or who is forced into manifestation of a serious adverse reaction or aggravation of concomitant immune disorder. Also, the amount of PB in a sample of a RRMS patient can be measured, thereby preferably selecting a patient suitable for treatment with an IL-6 inhibitor while providing a treatment method effective for a patient not suitable for IFN-β.

The invention claimed is:

1. A method for determining the therapeutic effect of an IL-6 inhibitor on a relapsing-remitting multiple sclerosis patient and treating the patient, the method comprising the steps of:
   (i) obtaining a biological sample from the patient with relapsing-remitting multiple sclerosis, wherein the biological sample comprises a whole blood or peripheral blood sample;
   (ii) measuring the amount of a plasmablast contained in the biological sample isolated from the relapsing-remitting multiple sclerosis patient;
   (iii) determining that the therapeutic effect of the IL-6 inhibitor is high when the amount of the plasmablast measured in the patient is high as compared with a healthy individual; and
   (iv) administering an amount of the IL-6 inhibitor to the patient effective to treat the relapsing-remitting multiple sclerosis in the patient exhibiting a high amount of plasmablast.

2. The method according to claim 1, wherein the IL-6 inhibitor is an anti-IL-6 receptor antibody.

3. The method according to claim 2, wherein the anti-IL-6 receptor antibody is a chimeric antibody, a humanized antibody, or a human antibody.

4. The method according to claim 1, wherein it is determined that the amount of a plasmablast is high when the ratio of the plasmablast to a $CD19^+$ B cell in the relapsing-remitting multiple sclerosis patient is 3.50% or more.

5. A method for treating relapsing-remitting multiple sclerosis (RRMS) in a subject highly expressing a plasmablast, comprising administering to the subject highly expressing the plasmablast a therapeutic agent comprising an amount of an IL-6 inhibitor effective to treat the RRMS in the subject.

6. The method according to claim 5, wherein the IL-6 inhibitor is an anti-IL-6 receptor antibody.

7. The method according to claim 6, wherein the anti-IL-6 receptor antibody is a chimeric antibody, a humanized antibody, or a human antibody.

* * * * *